(12) United States Patent
Meloul

(10) Patent No.: US 7,083,600 B2
(45) Date of Patent: Aug. 1, 2006

(54) SAFETY NEEDLE AND SHIELD

(75) Inventor: Raphael F. Meloul, Atlanta, GA (US)

(73) Assignee: Advanced Medical Sharps, Inc., Norcross, GA (US)

( * ) Notice: Subject to any disclaimer, the term of this patent is extended or adjusted under 35 U.S.C. 154(b) by 0 days.

(21) Appl. No.: 10/635,503

(22) Filed: Aug. 7, 2003

(65) Prior Publication Data

US 2004/0102740 A1    May 27, 2004

Related U.S. Application Data

(60) Provisional application No. 60/405,979, filed on Aug. 26, 2002, provisional application No. 60/402,487, filed on Aug. 8, 2002.

(51) Int. Cl.
*A61M 5/00* (2006.01)
(52) U.S. Cl. ................ 604/263; 604/110; 128/919
(58) Field of Classification Search ............ 604/110, 604/181, 192, 198, 272; 128/919
See application file for complete search history.

(56) References Cited

U.S. PATENT DOCUMENTS 5,336,199 A * 8/1994 Castillo et al. ............. 604/198
6,524,276 B1   2/2003 Halseth et al.

* cited by examiner

*Primary Examiner*—Kevin C. Sirmons
(74) *Attorney, Agent, or Firm*—Smith Frohwein Tempel Greenlee Blaha LLC; Gregory Scott Smith

(57) ABSTRACT

A safety needle includes a needle with a sharp end and a needle shield. The needle shield includes collapsible interlocking members, wherein one member is an end member with a hole surrounding the needle, a spring inside the collapsible interlocking members that applies an expanding force on the collapsible interlocking members, a releasable latch structure that retains the collapsible interlocking members in a collapsed state, wherein when the releasable latch structure is actuated the collapsible interlocking members expand and enclose the sharp end of the needle, and a closing structure that prevents the sharp end of the needle from exiting the hole after the collapsible interlocking members enclose the sharp end of the needle.

2 Claims, 34 Drawing Sheets

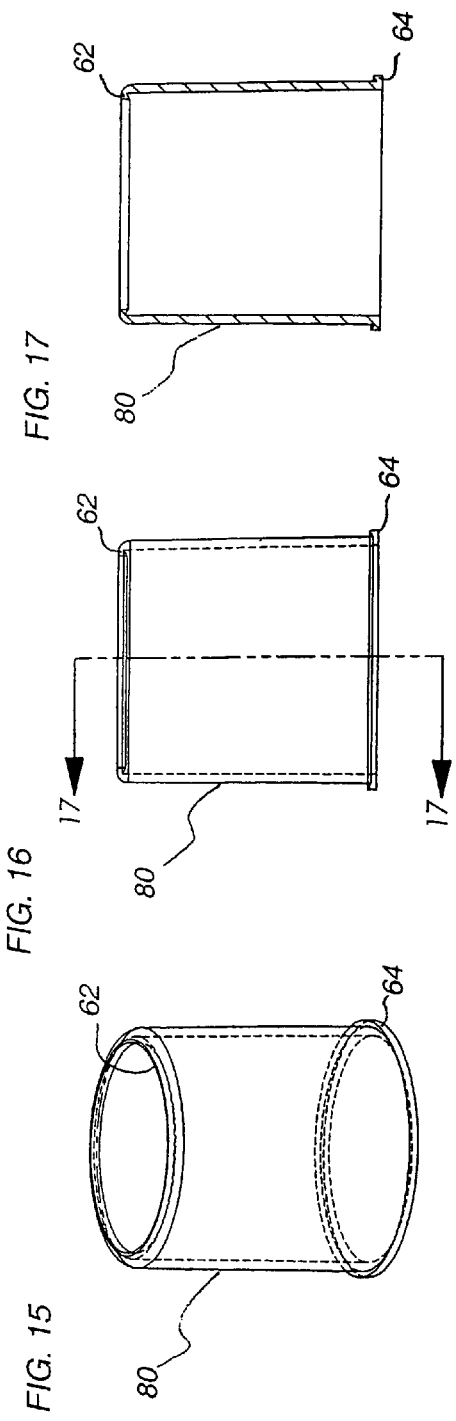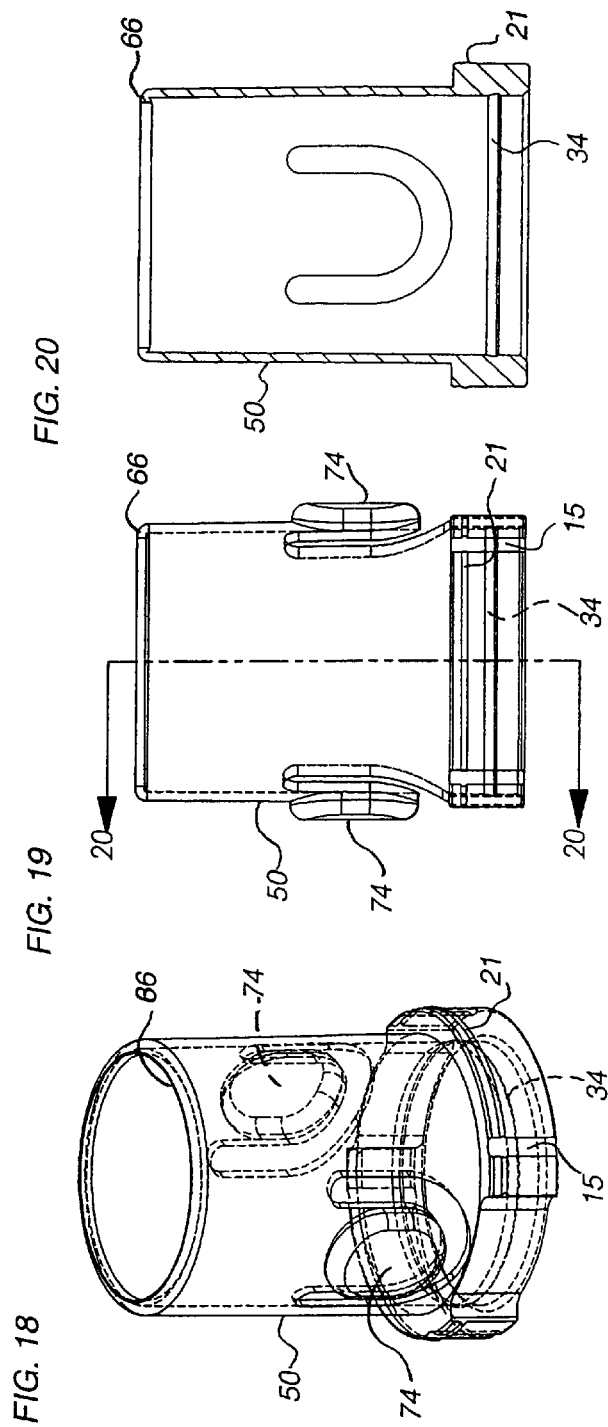

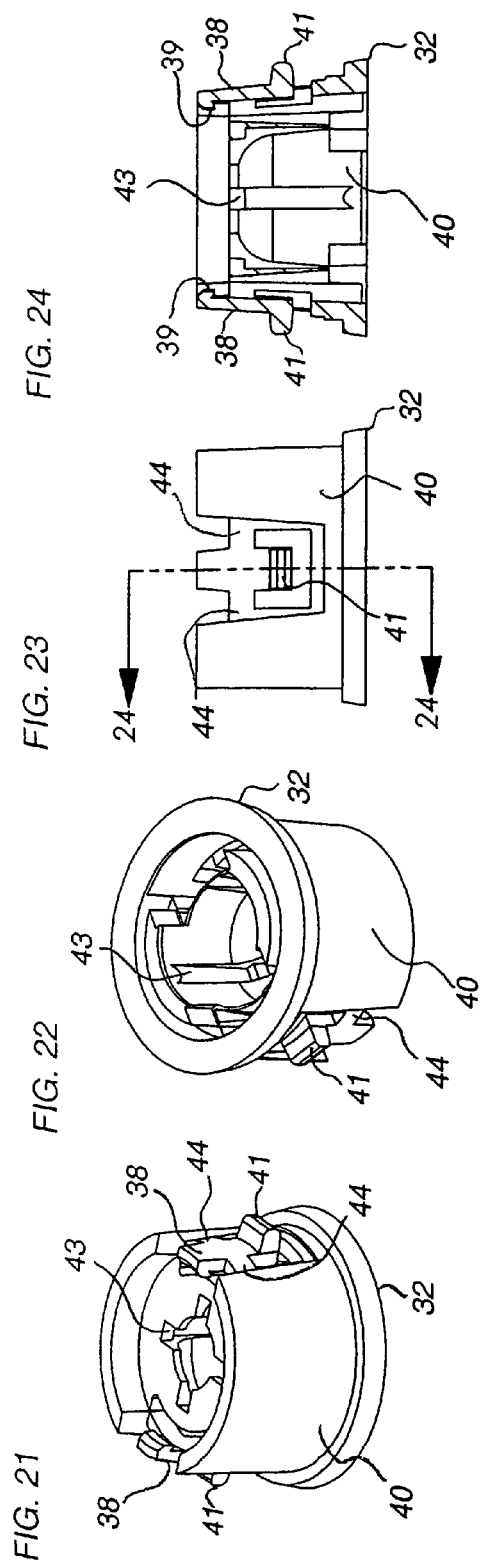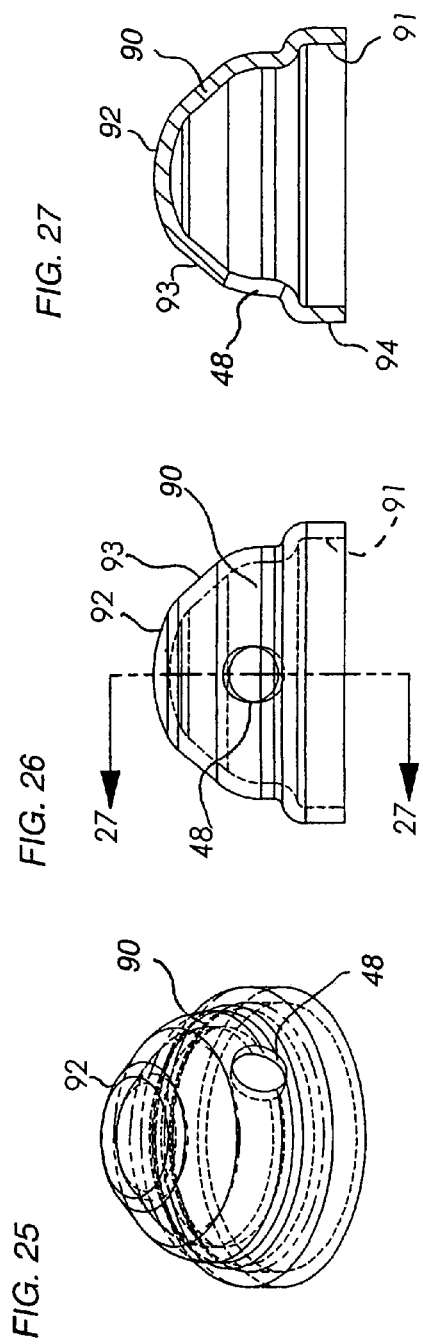

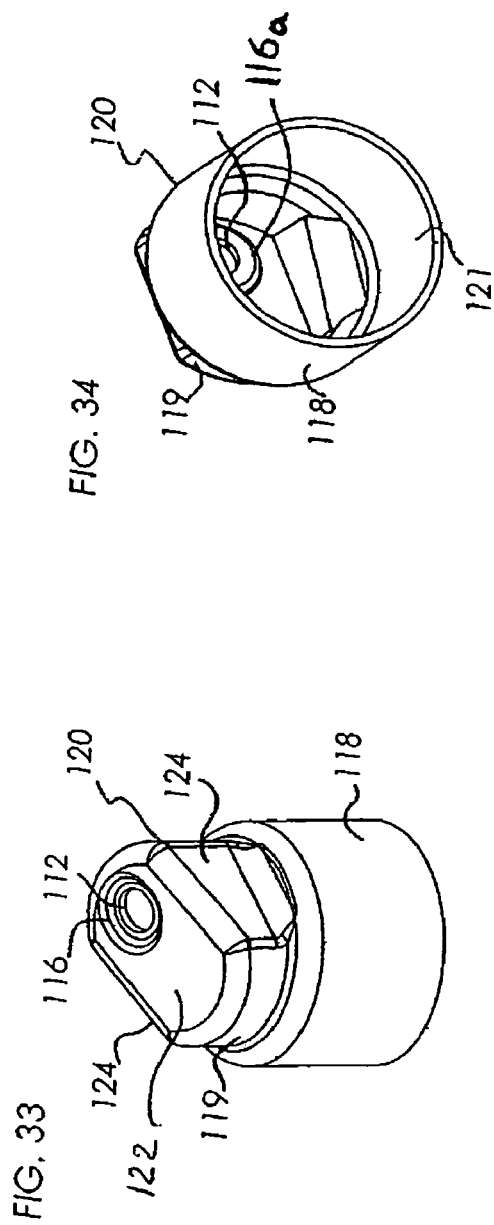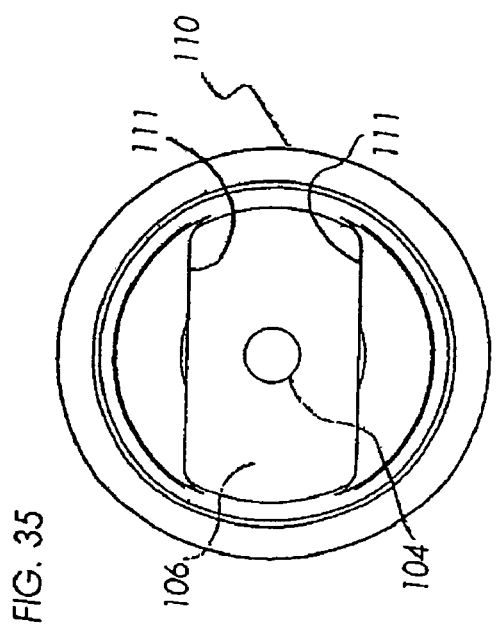

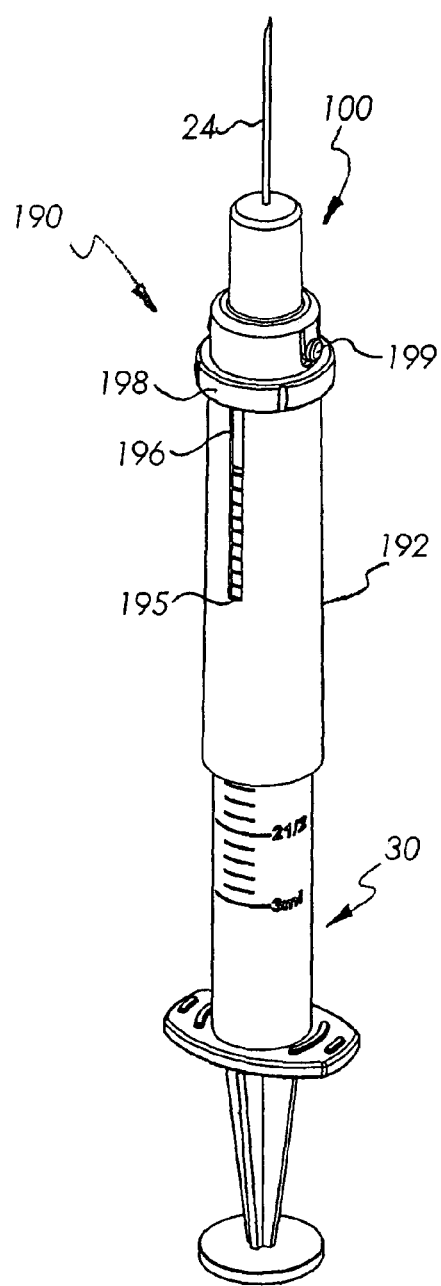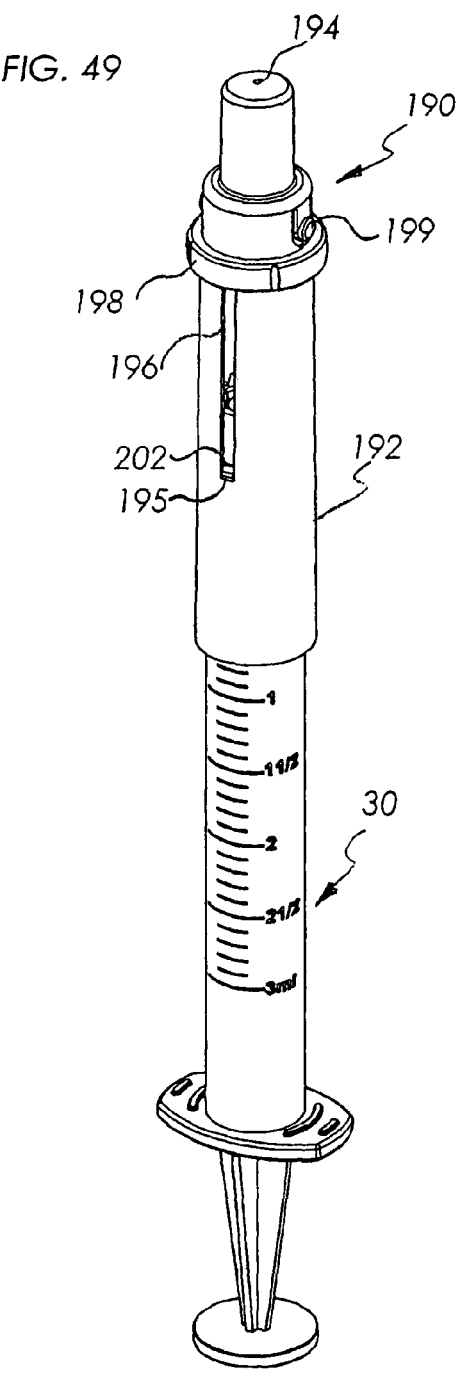

FIG. 50
FIG. 51
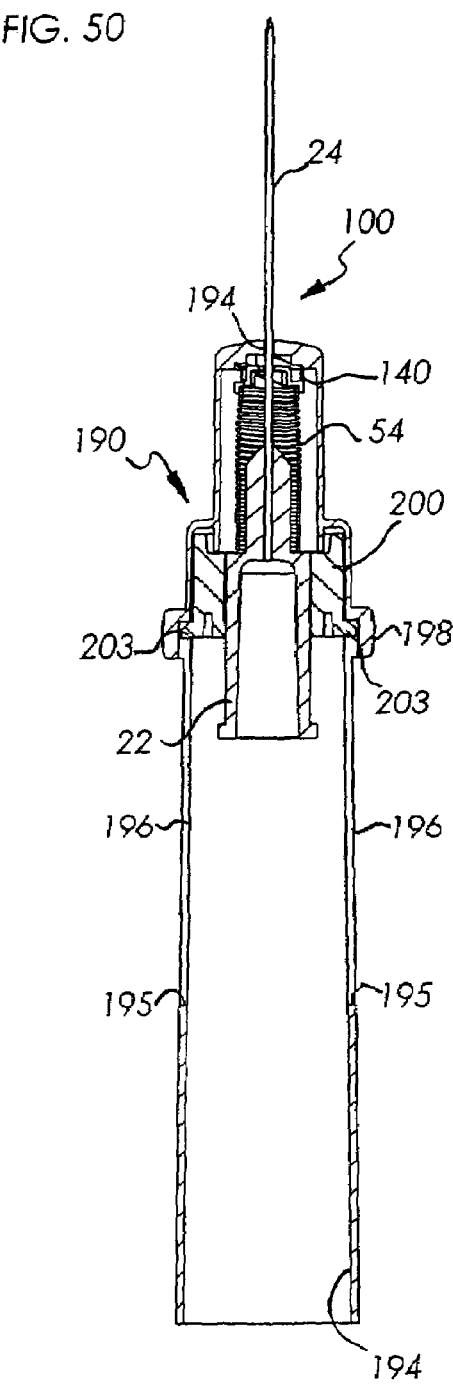
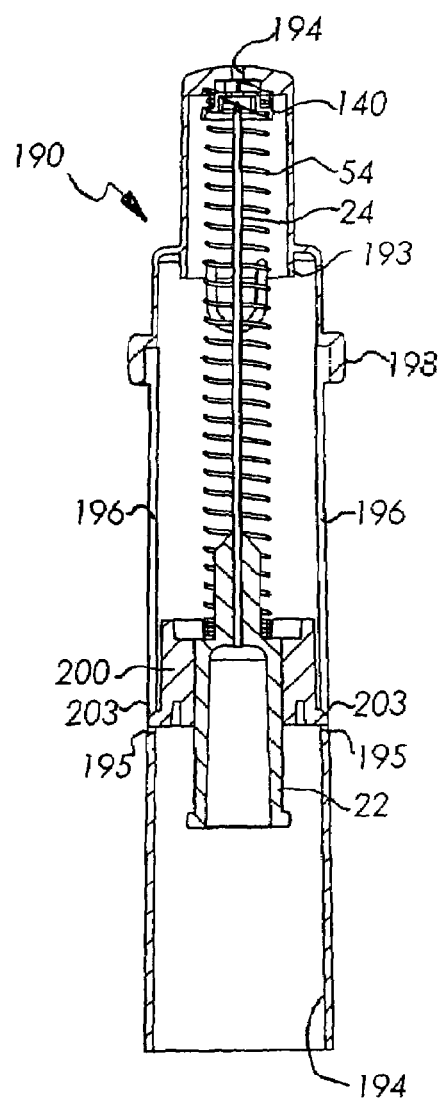

SAFETY NEEDLE AND SHIELD

This application claims the benefit of United States Provisional Patent Application Nos. 60/402,487, filed on Aug. 8, 2002 and 60/405,979, filed on Aug. 26, 2002, the entirety of which is hereby incorporated by reference for all purposes as if fully set forth herein.

BACKGROUND OF THE INVENTION

The present invention relates to a safety needle, which comprises a hypodermic needle equipped with a safety shield to guard healthcare workers from accidental needlestick injuries.

In addition the shield completely encapsulates the needle and any contaminants that may be on it. More specifically, the invention relates to a hypodermic needle with deployable a shield deployed upon and during retraction of needle. The present invention may be used for example with IV infusion sets, blood collection devices, insulin syringes, dental syringes, and the administration of medication by syringe and hypodermic needles.

Needlestick injuries in the U.S. cost 1.6 billion annually and are a source of immeasurable suffering. This cost is associated with the preventive treatment administered to healthcare workers experiencing a needlestick injury and the treatment of healthcare workers actually infected due to the injury. An additional burden to the establishment is through lost working days and in the case of infection the replacement of healthcare workers not able to return to the workforce.

In response to this growing problem, the needlestick prevention mandate, Bill 13-266 was passed by congress in October 2000 and became effective Apr. 18, 2001. The Needlestick Safety Prevention Act H.R 5178 law 106 430 was passed into law on Nov 6, 2000. The need for a safer needlestick prevention product, combined with the needlestick prevention mandate, creates a need for a cost effective means of preventing needlestick injuries. The healthcare communities adoption and compliance with the mandate has created a growing demand for safer needles.

When administering medication or drawing blood from potentially infected individuals, standard needle and syringe arrangements leave the healthcare worker exposed to contaminated needles during recapping and transfer to a sharps container and thereby expose the healthcare professional to the danger of a needlestick injury and exposure to contagious diseases such as HIV, TB, Hepatitis as well as many other diseases. Another reported high risk of accidental needle pricks is the recapping of the needle before disposal. In some cases, it has been reported that the needle punctured through the sidewall of the cap and punctured the finger holding the cap. In the last few years many new safety syringes have been introduced on the market, most requiring the complete retooling of the existing syringes, adding cost and delaying the introduction of those safety syringes. The many designs available results in additional inventory due to the multiple product combinations thereby increasing cost. These safety syringes have permanently attached needles of varying lengths, needle gage and volume capacity. Due to the dramatic departure from the standard syringe arrangement more comprehensive training is also required. All these factors combined with the need for additional training has added cost to healthcare and may discourage the use of safety syringes and slow the adoption of their use.

With this invention the safety is built into the needle, this does not affect any of the products that may need to work with the syringe or the hypodermic needle. There is no change in the number of parts the hospital has to inventory. The safety needle of the present invention has the ability to adapt to all syringes regardless of volume capacity.

The proposed invention will address each of the objections to and limitations of existing safety syringes and safety needles.

SUMMARY OF THE INVENTION

Accordingly, the present invention is directed to a safety needle and shield and to draw blood that substantially obviates one or more of the problems due to limitations and disadvantages of the related art.

An advantage of the present invention is to provide a needle shield assembly for use with a needle cannula, such as a hypodermic needle. The needle cannula may be of prior art construction and includes proximal and distal ends with a lumen extending continuously between the proximal and the distal ends as to accommodate a fluid flow.

The distal end of the needle may be beveled to define a point. The proximal end of the needle cannula may be mounted to a structure for enabling fluid flow through the lumen.

In a preferred embodiment, as described and illustrated herein, the proximal end of the needle cannula is securely connected to a needle hub. The needle hub may include structures for releasable attachment to a medical device, such as hypodermic syringe barrels, IV infusion sets and blood collection devices. In other embodiments the needle cannula may be mounted directly in a medical implement such as hypodermic syringe barrel, IV infusion set, blood collection devices and many other devices using needles in a medical instrument.

Prior to use the needle has a plastic cap to prevent accidental needlestick from the unused needle, the needle cap is removed and the needle is exposed in preparation for use. At this stage the needle shield is in a retracted position at the proximal end of the needle, leaving the needle exposed and ready for use. A feature of this invention is for the retracted shield not to obstruct the line of view to the injection site. Another feature of this invention is to allow for activation of the safety shield without dispensing all the content of the syringe. Yet another feature of the invention is the one handed activation of the finger actuated pads, this ability minimizes the risk associated with the two handed activation used by other marketed products. Another risk lowered with this invention is that the activation does not require being in the proximity of the contaminated needlepoint when activating the safety shield.

After use preferably while the needle is still engaged in the injection site, the shield is activated by applying pressure to the finger actuation pads, causing the interlocked tubular segments to deploy and completely encapsulate the needle so as to cover the entire needle, therefore shielding the health care worker from the risk of needlestick injury and exposure to contaminated fluids and other contaminants that may be present on the needle cannula.

The needle shield assembly of the subject invention includes a release ring with latches, a cylindrical actuation component with releasing features, a number of cylindrical axially aligned components that when dispensed form an elongated interlocked assembly around the needle component and a safety cap all constructed of polyethylene or other injection moldable plastic. A spring made of stainless steel and a cap made of stainless steel or may also be injection molded from a hard plastic.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a safety needle includes a needle with a sharp end and a needle shield. The needle shield includes collapsible interlocking members, wherein one member is an end member with a hole surrounding the needle, a spring inside the collapsible interlocking members that applies an expanding force on the collapsible interlocking members, a releasable latch structure that retains the collapsible interlocking members in a collapsed state, wherein when the releasable latch structure is actuated the collapsible interlocking members expand and enclose the sharp end of the needle, and a closing structure that prevents the sharp end of the needle from exiting the hole after the collapsible interlocking members enclose the sharp end of the needle.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 15 shows an isometric view of an exemplary third cylindrical segment;

FIG. 16 shows a side elevation view of an exemplary third cylindrical segment.

FIG. 17 shows a cross sectional side elevation view of an exemplary third cylindrical segment.

FIG. 18 shows an isometric view of an exemplary fourth cylindrical segment.

FIG. 19 shows a side elevation view of an exemplary fourth cylindrical segment;

FIG. 20 shows a cross sectional side elevation view of an exemplary fourth cylindrical segment;

FIG. 21 shows a top isometric view of an exemplary release ring;

FIG. 22 shows a bottom isometric view of an exemplary release ring;

FIG. 23 shows a side elevation view of an exemplary release ring;

FIG. 24 shows a cross sectional front elevation view of an exemplary release ring;

FIG. 25 shows a top isometric view of an exemplary steel cap;

FIG. 26 shows a side elevation view of an exemplary steel cap;

FIG. 27 shows a cross sectional front elevation view of an exemplary steel cap;

FIG. 33 shows a top isometric view of an exemplary steel cap;

FIG. 34 shows a bottom isometric view of an exemplary steel cap;

FIG. 35 shows a bottom view of an exemplary first most distal cap for the slide cap version;

FIG. 48 shows an isometric view of an exemplary one-cap version un-deployed;

FIG. 49 shows an isometric view of an exemplary one-cap version deployed;

FIG. 50 shows an enlarged cross sectional side elevation view of an exemplary one-cap version un-deployed;

FIG. 51 shows an enlarged cross sectional side elevation view of an exemplary safety needle of the one-cap version deployed;

DETAILED DESCRIPTION OF THE ILLUSTRATED EMBODIMENTS

Reference will now be made in detail to an embodiment of the present invention, example of which is illustrated in the accompanying drawings.

Figure 1:
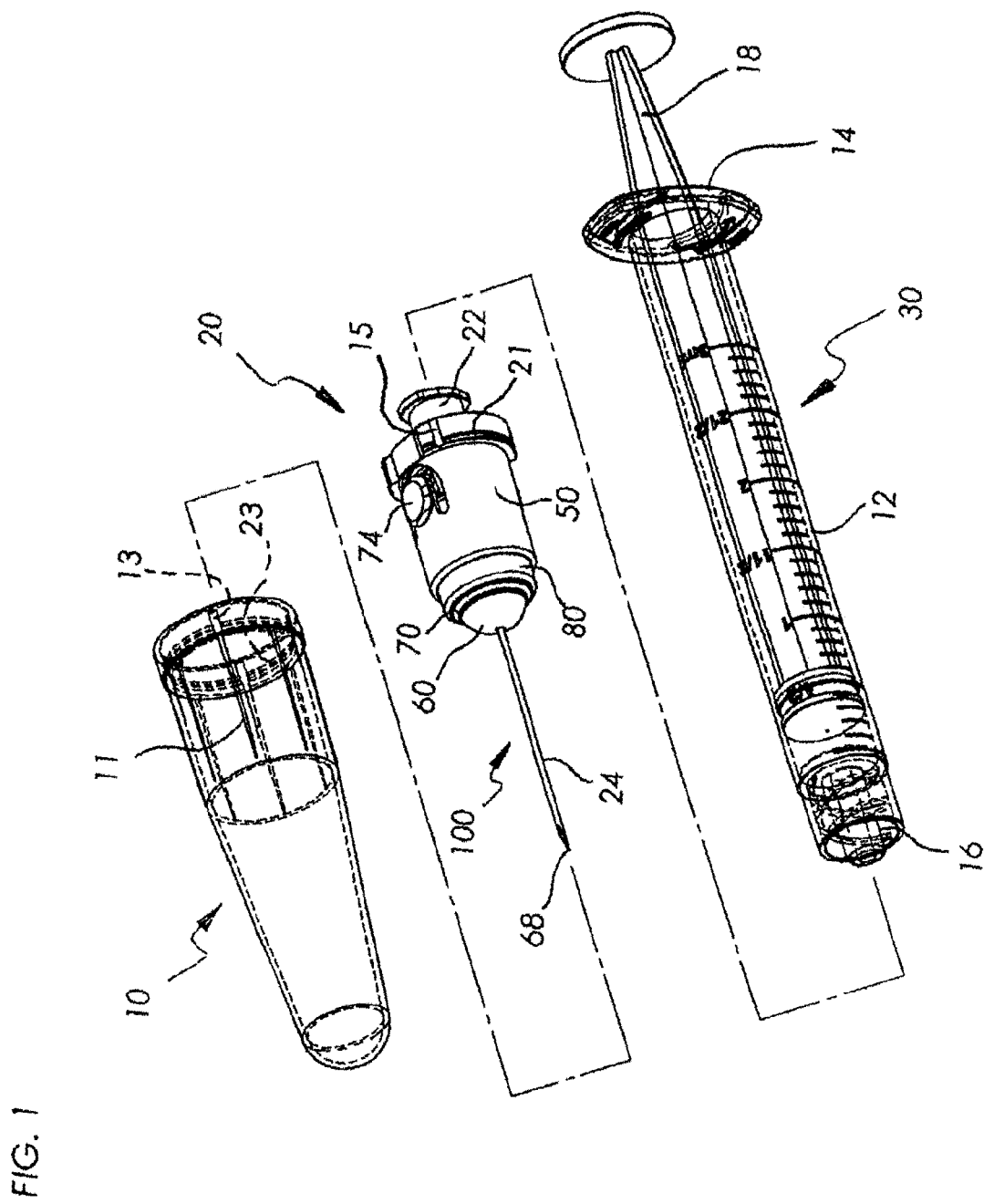
FIG. 1 is an exploded isometric view of an exemplary safety needle, cap and a standard hypodermic syringe equipped with a standard luer lock male hub. The safety needle is in an un-deployed state.
Figure 56:
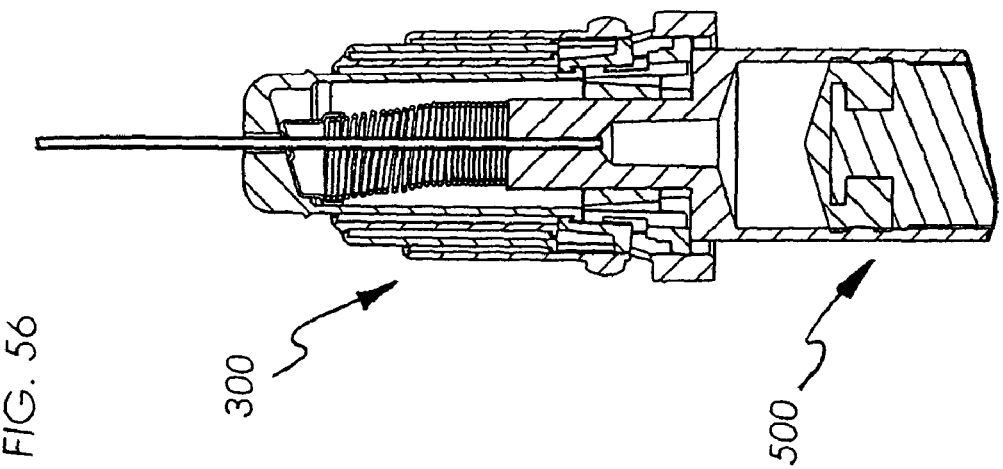
FIG. 56 shows an enlarged partial cross sectional side elevation view of an exemplary safety needle of the present invention, rigidly attached to a syringe, having a rigidly attached hypodermic needle.

FIG. 1 shows a needle shield assembly 20 in accordance with one embodiment of the present invention. The needle shield assembly 20 has a needle assembly 100 that includes a hypodermic needle cannula 24 and a needle hub 22. The needle cannula 24 has a distal end 68 that is beveled to define a sharp tip, and a proximal end rigidly attached to needle hub 22. An opening extends between the proximal and distal ends of the needle cannula 24 for dispensing fluid through needle cannula 24. A safety cap 10 covers the needle cannula 24 before use. All the following embodiments of the present invention may include a hypodermic needle and hub or a syringe having a hypodermic needle rigidly affixed to its distal end as illustrated in FIG. 56.

Figure 2:
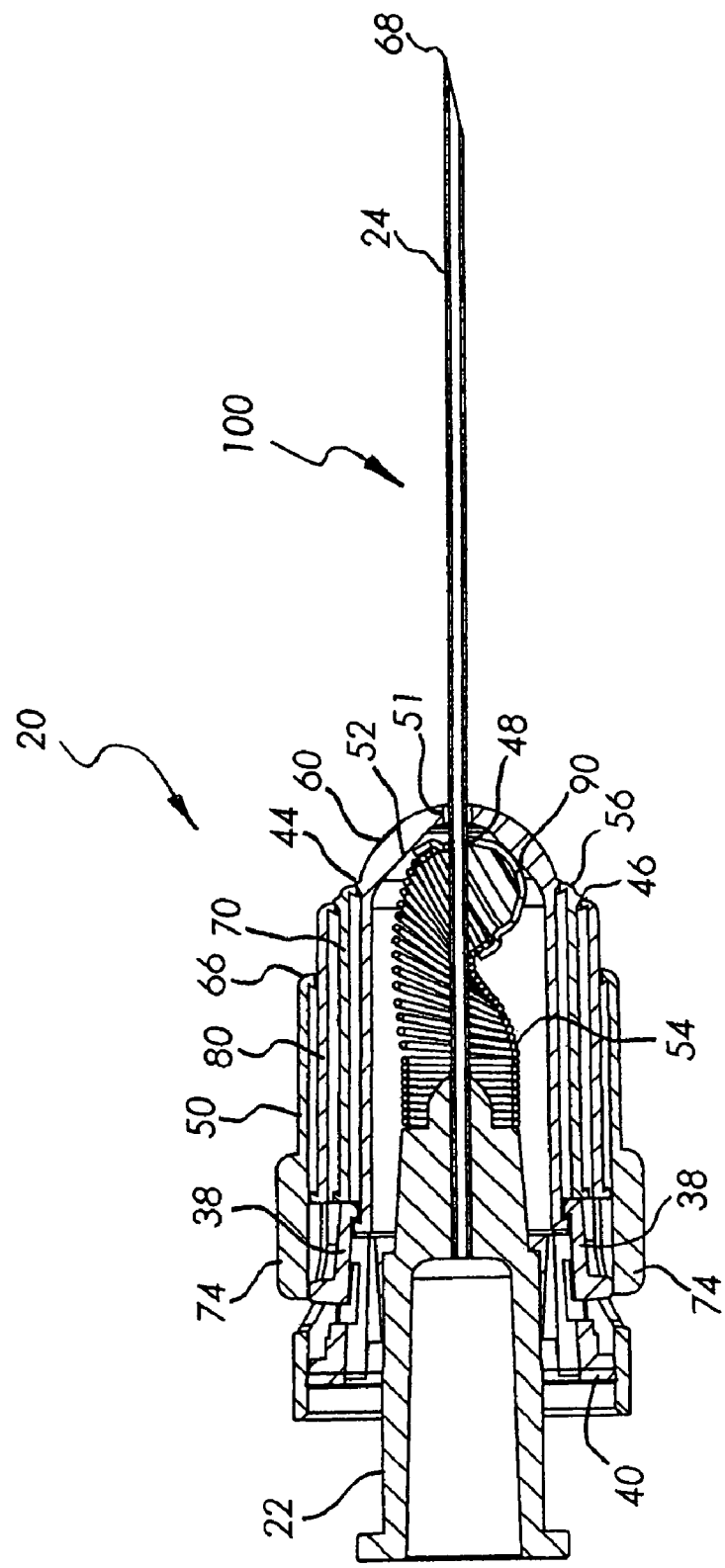
FIG. 2 shows an enlarged side elevation cross sectional view of an exemplary hypodermic needle and safety shield before deployment. The needle is ready for use.

The needle shield assembly 20 as seen in FIG. 2 includes a retaining structure including a release ring 40 with latches 38, a cylindrical actuation component 50 with releasing features 74, and cylindrical axially aligned components 60, 70 and 80. When dispensed, the cylindrical components 60, 70, 80 form an elongated interlocked assembly around the needle component 24 and may be constructed of polyethylene or other injection moldable plastic. Inside the cylindrical components 60, 70, 80 is a spring 54 and a cap 90. The spring 54 and cap may be made of stainless steel. The cap 90 may also be injection molded from a hard plastic.

Figure 30:
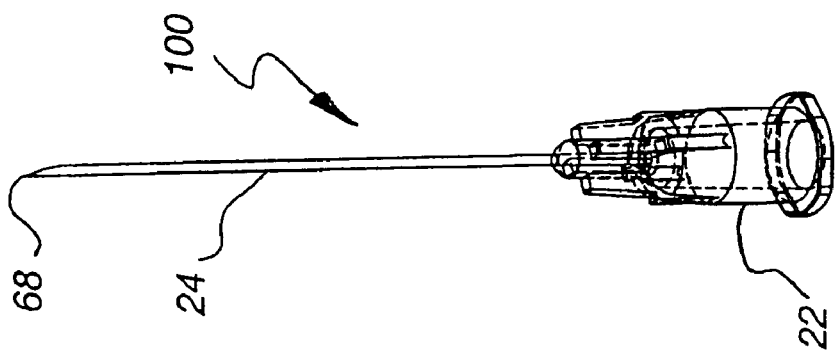
FIG. 30 shows a top isometric view of a hypodermic needle with cap.
Figure 29:
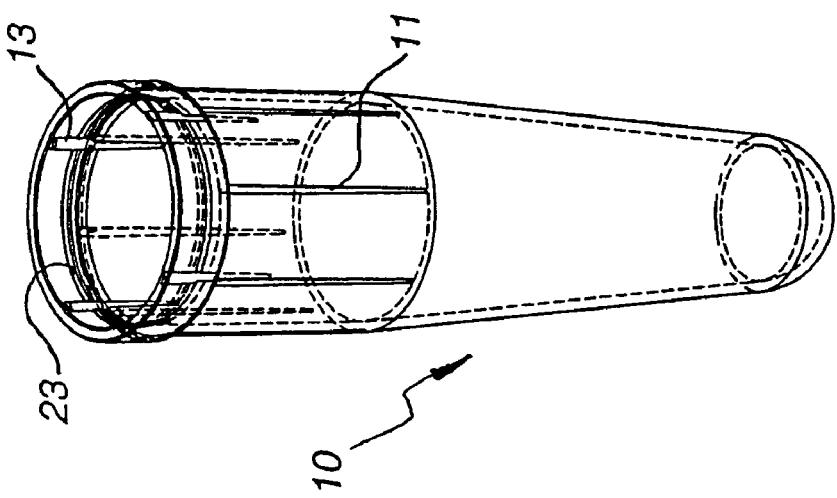
FIG. 29 shows a bottom isometric view of an exemplary plastic safety cap.
Figure 28:
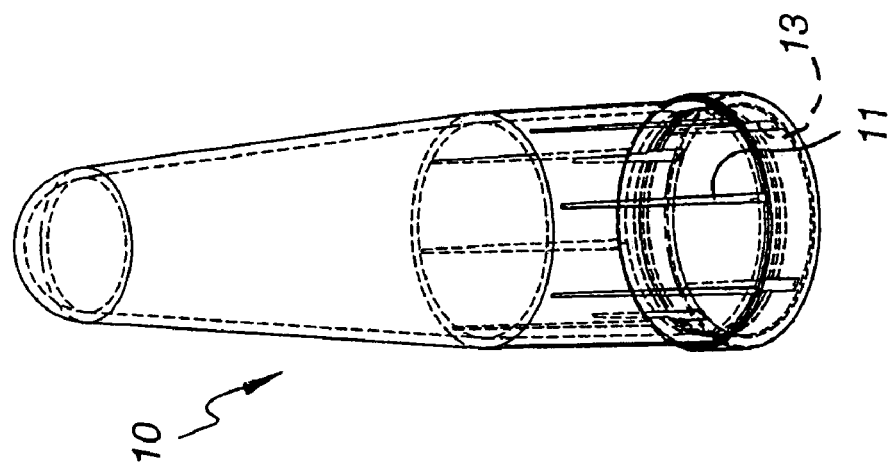
FIG. 28 shows a top isometric view of an exemplary plastic.

FIGS. 21–24 show a release ring 40 as a substantially rigid elongated structure having a proximal and a distal end and having an opening 43, extending continuously between the proximal and the distal ends. The opening 43 in release ring 40 has an appropriate shape to be rigidly connected with a hub 22 of hypodermic needle 100 as shown in FIG. 30. Another feature of release ring 40 are two latches 38 diametrically opposed having a distal end with hooks 39 extending in the direction of the proximal end of release ring 40. The hook feature 39 faces toward a central axis of release ring 40. The hook 39 of latch 38 is engaged with the proximal retaining ring 42 (FIG. 3) of the first cylindrical component 60. The proximal part of latch 38 has a heel feature 41 with the heel facing away from the central axis of release ring 40. The entirety of the latch feature is pivotable when pressed upon with the actuation pads 74 (FIG. 2) of actuation component 50 (FIG. 2). A feature of this invention is the ability to modify the latch pivot to cause it to become disabled after actuation of the needles shield assembly 20 to prevent rearming of needle 24. The number of latches 38 may be varied depending upon the size of the device and the end use application. Yet another feature of the release ring 40 is a locking ridge 32 positioned at the most proximal end of the external surface of release ring 40 that rigidly connects the release ring and cylindrical actuation component 50 shown in FIGS. 18–20.

The cylindrical actuation component 50 shown in FIGS. 18–20 has a cylindrical substantially rigid elongated tubular structure having a proximal and a distal end and having an opening aligned with the axis of the actuation component extending continuously between the proximal and the distal ends of the actuation component. Another feature of the actuation component 50 is a locking groove 34 positioned on the inside proximal surface of the opening and centered with the axis of the component so as to attach rigidly to locking the ridge 32 on release ring 40. The actuation component 50 has finger-actuated pads 74 positioned diametrically opposed and in alignment with the heel features 41 of release ring 40. A keying tab 203, shown in FIG. 53 but not implemented in release ring 40 may also be implemented to align actuation pads 74 with the heel features 41 of release ring 50. When pressed, pads 74 apply pressure on the heels 41 of latches 38 so as to displace the latches in release ring 40 causing the latches 35 to pivot and release the first cylindrical component 60, thereby deploying all shield cylindrical components 60, 70, 80. Yet another feature of the actuation component 50 is an annular structure 66 on the most distal internal surface of the actuation component, used as a retaining ring so as to keep the third most distal component 80 from deploying beyond the actuation component 50.

The third cylindrical component 80 shown in FIGS. 15–17 is a substantially rigid elongated tubular structure having a proximal and a distal end and having an opening aligned with the axis of actuation component 50 extending continuously between the proximal and the distal ends of the third most distal component. Another feature of third most distal component 80 are two annular structures used as retaining rings; one 62 being at the most distal internal surface of the component; the other 64 being on the most proximal external surface of the component. The most distal annular ring 62 serves as a stop to prevent the second cylindrical component 70 from advancing past the third cylindrical component 80. The most proximal annular ring 64 serves as a stop to prevent the third cylindrical component 80 from advancing past the actuation component 50.

Figure 12:
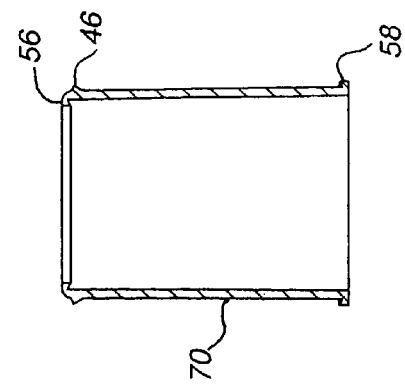
FIG. 12 shows an isometric view of an exemplary second most distal segment.
Figure 13:
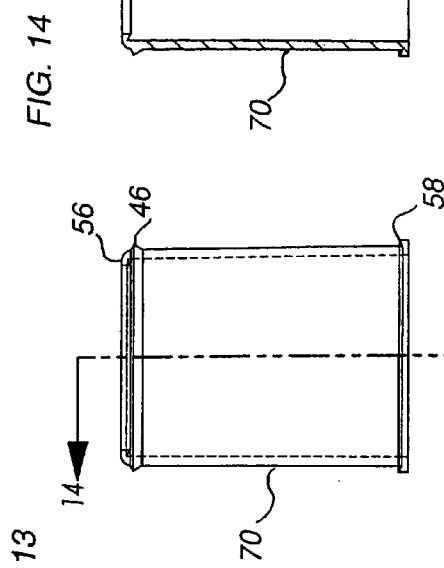
FIG. 13 shows a side elevation view of an exemplary second cylindrical segment.
Figure 14:
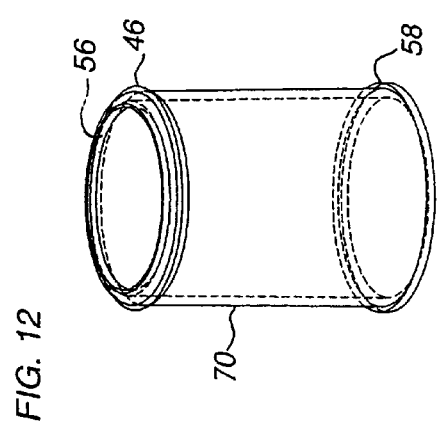
FIG. 14 shows a cross sectional side elevation view of an exemplary second cylindrical segment.

The second cylindrical component 70 shown in FIGS. 12–14 is a substantially rigid elongated tubular structure having a proximal and a distal end and having an opening aligned with the axis of actuation component 50 extending continuously between the proximal and the distal ends of the second cylindrical component. Another feature of the second cylindrical component 70 are two annular structures used as retaining rings; one 56 being at the most distal end of the internal surface of the component 70; the other 58 being on the most proximal end of the external surface of the component. The most distal annular ring 56 serves as a stop to prevent the first cylindrical component 60 from advancing past the second cylindrical component 70. The most proximal annular ring 58 serves as a stop to prevent the second cylindrical component 70 from advancing past the third cylindrical component 80. Another feature of second cylindrical component 70 is an external annular ring 46 on the distal outer surface of second cylindrical component 70. The annular ring 46 serves as a stop to prevent the third cylindrical component 80 from advancing past the second cylindrical component 70.

Figure 9:
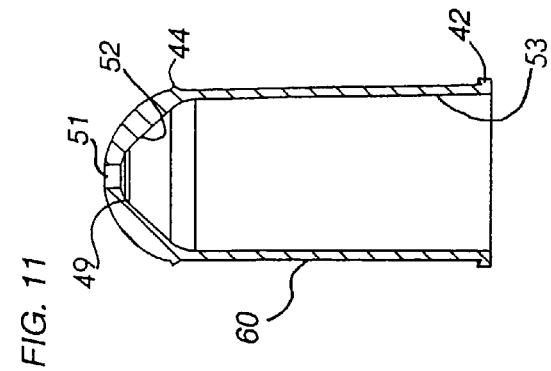
FIG. 9 shows an isometric view of an exemplary first most distal segment.
Figure 10:
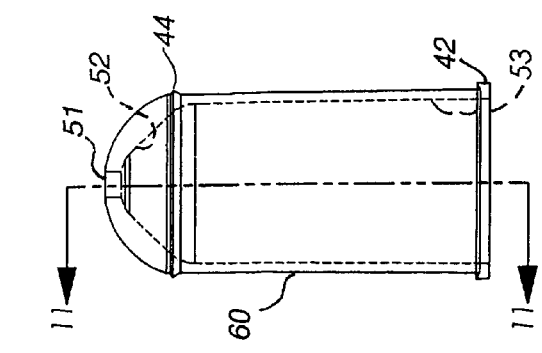
FIG. 10 shows a side elevation view of an exemplary first cylindrical segment.
Figure 11:
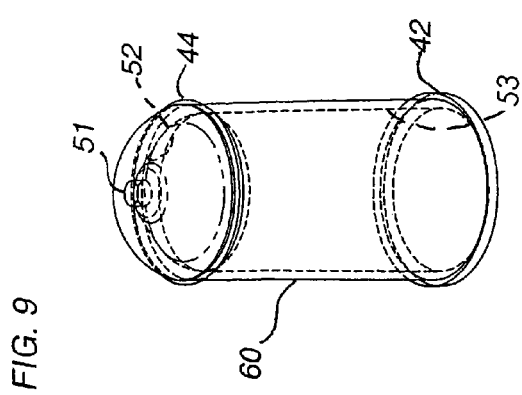
FIG. 11 shows a cross sectional side elevation view of an exemplary first cylindrical segment.

FIGS. 9–11 show an embodiment of the first cylindrical component 60. The first cylindrical component 60 is a substantially rigid elongated tubular structure having a proximal and a distal end and having an opening aligned with the axis of the actuation component 50 extending continuously between the proximal and the closed distal end of the first cylindrical component 60. Another feature of the first cylindrical component is an annular structure 42 used as a retaining ring. The annular structure is on the most proximal end of the external surface of component 60 so as to prevent the first cylindrical component 60 from advancing past the second cylindrical component 70. Another feature of the first cylindrical component 60 is an external annular ring 44 positioned on the distal outer surface of the first cylindrical component 60 so as to prevent the second cylindrical component 70 from advancing past the first cylindrical component 60. Another feature of the first cylindrical component 60 is an annular opening 51 in the cylindrical part of the first cylindrical component 60 and having its axis in alignment with the axis of the first cylindrical component so as to allow the needle cannula 24 to pass through it. Yet another feature of the first cylindrical component 60 is a surface positioned at the most distal end of the internal opening having a domed concave surface 52 and joining the walls 53 of the opening in the first most distal component. This feature is especially useful when a flip cap component 90 is used.

The flip cap component 90 shown in FIGS. 25–27 is a substantially rigid elongated domed structure having a proximal and a distal end and having an opening 91 aligned with the axis of the actuation component 50 extending continuously between the proximal and the closed distal end of the flip cap 90. The flip cap 90 is a part of a closing structure that prevents the needle cannula 24 from extending out of the needle shield assembly 20 after deployment of the need shield assembly 20. A feature of the flip cap is a domed surface 92, being the most distal surface of the flip cap 90 similar to the domed surface 52 of first cylindrical component 60 of FIGS. 9–11. Another feature of the flip cap 90 is an annular opening 48 on the domed surface 92, positioned at an angle from the center axis of the flip cap 90. The flip cap 90 may have a larger tubular section 94 extending proximally and having its distal end merge with the domed portion 92 of the flip cap 90, and forming a recessed area 91 for the spring 54 to nest into. A second purpose of the tubular section 94 is to form a barrier around the needlepoint 68 for added protection. The flip cap 90 may have a tab 28 extending inwardly from the larger tubular segment 94 of the flip cap 90 to secure the spring 54 to the flip cap 90.

Figure 3:
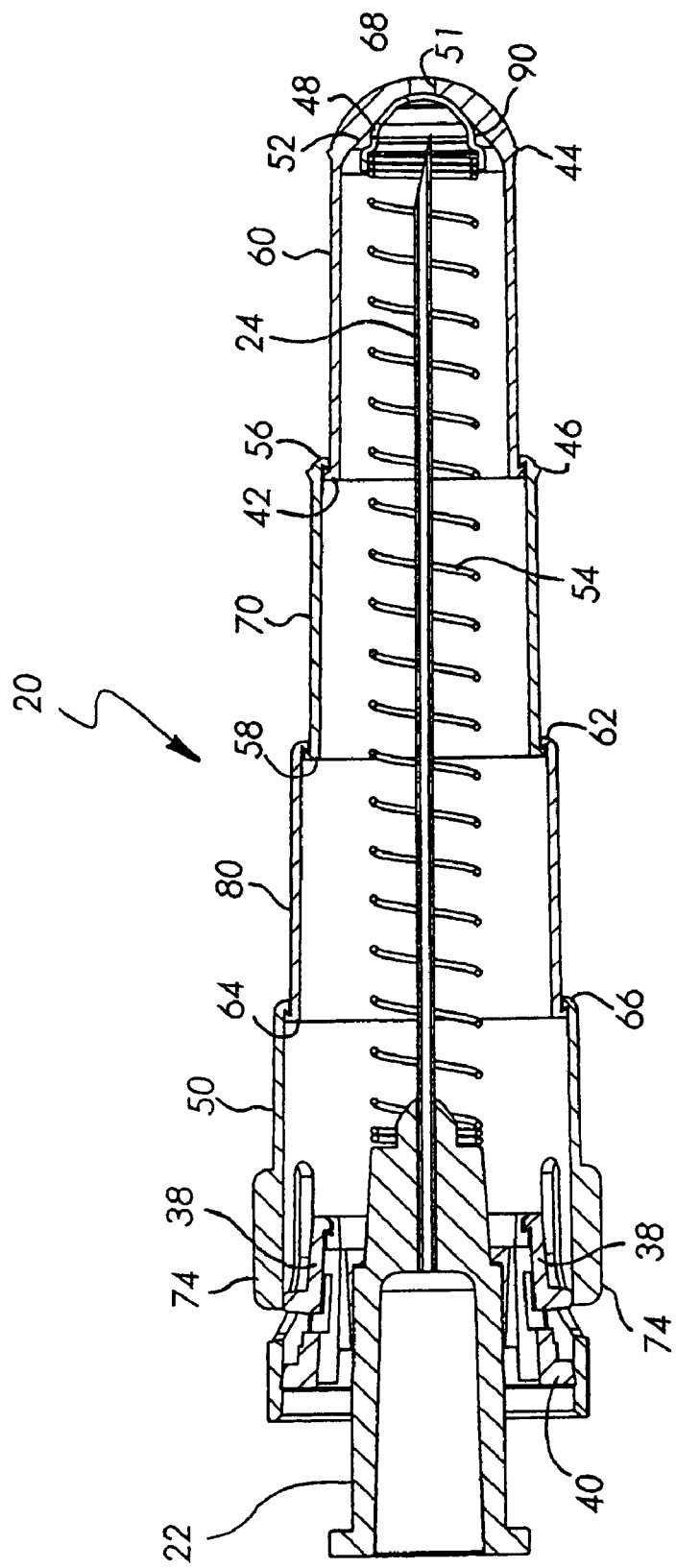
FIG. 3 shows an enlarged cross sectional view of an exemplary hypodermic needle and safety shield after deployment wherein the needle has been used and the shield is deployed, and the needle is no longer a danger.
Figure 3A:
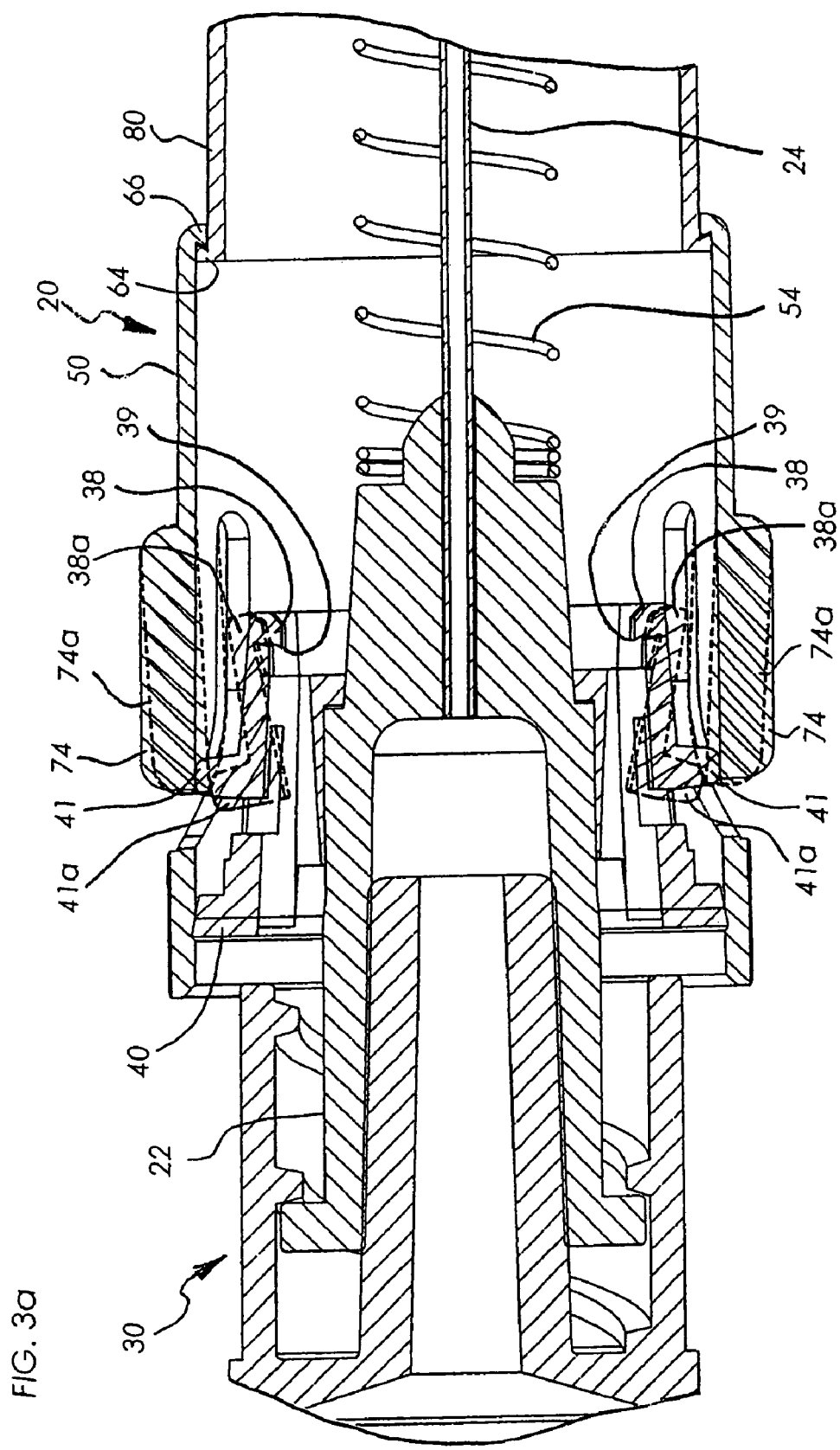
FIG. 3a shows a partial enlarged cross sectional view of an exemplary hypodermic needle, hub, and safety shield, attached to a standard hypodermic syringe, after deployment, wherein the actuation pads and latches are shown in solid lines before actuation and in dashed lines after actuation.
Figure 4:
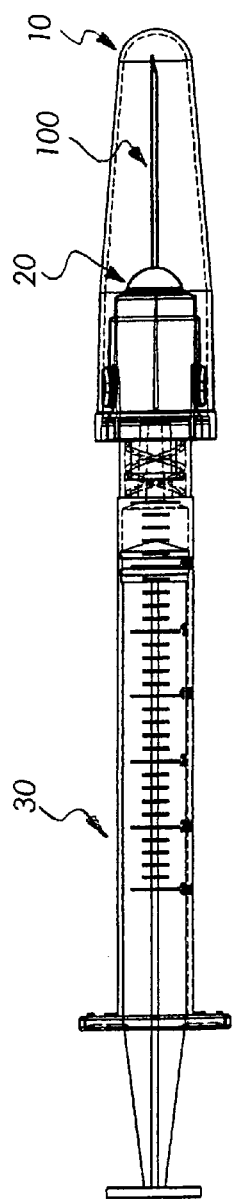
FIG. 4 shows a side elevation view of an exemplary safety needle with the safety cap attached to a conventional syringe.
Figure 5:
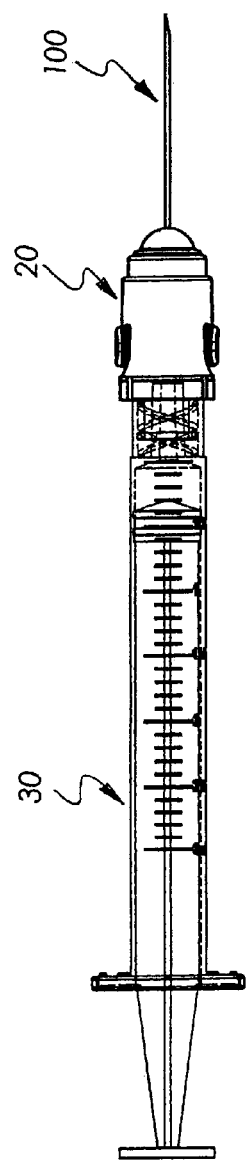
FIG. 5 shows a side elevation view of an exemplary safety needle with the safety cap removed attached to a conventional syringe and ready for use.
Figure 6:
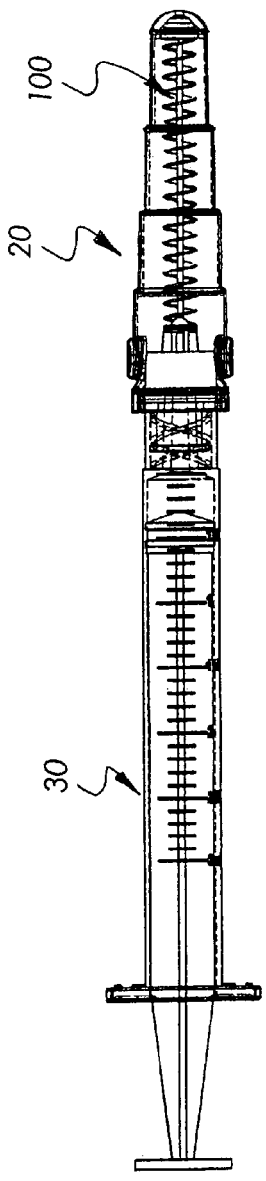
FIG. 6 shows a side elevation view of an exemplary safety needle with safety cap removed attached to a conventional syringe with the shield deployed after use.
Figure 8:
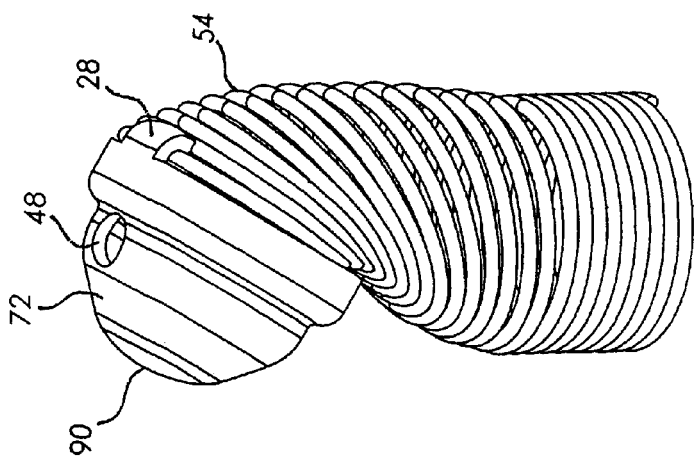
FIG. 8 shows an isometric view of an exemplary steel cap and spring before deployment, wherein the needle (not shown) is placed through hole 48.
Figure 7:
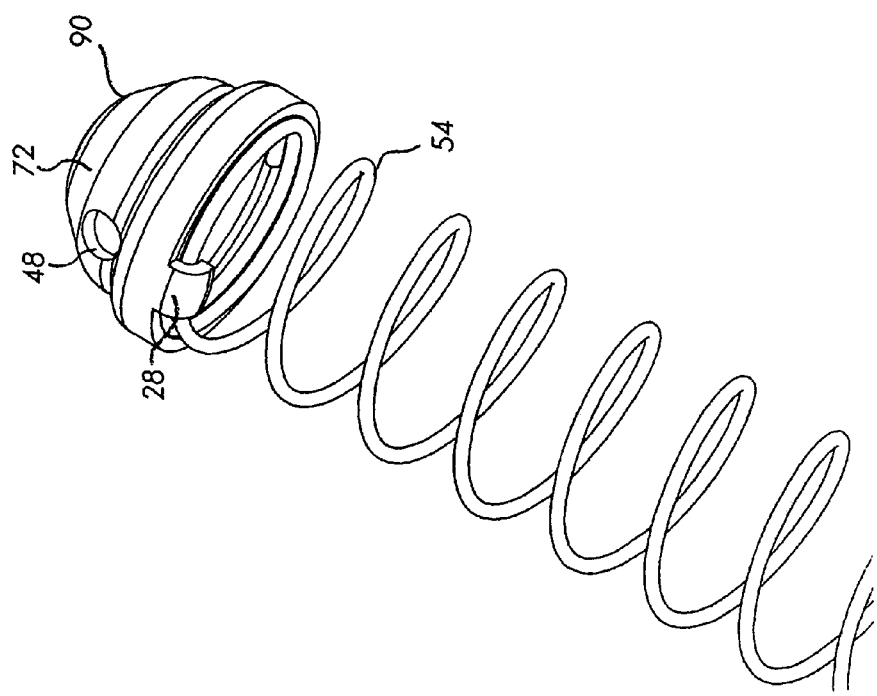
FIG. 7 shows an isometric view of an exemplary steel cap and spring after deployment, wherein the needle (not shown) has been repositioned so that it is now within the cap rather than in hole 48.

FIG. 3 shows the spring 54 as a conventional compression spring in a position substantially centered with the axis of needle cannula 24 with the proximal end of the spring resting against the distal end of needle hub 22 and the distal end of the spring nested in the recessed tubular portion 91 of flip cap 90. In addition spring 54 may optionally be secured by a tab in flip cap 90. The spring 54 is shown in a constant compressed state.

The operation of the flip cap 90 embodiment of the present invention will now be described. As shown in FIG. 2, the needle shield assembly 20 is attached to a syringe. The needle shield assembly 20 is in a compressed state with the first, second, and third cylindrical components 60, 70, 80 collapsed and nested within each other. The latch 38 engages the first cylindrical component 60 and holds the first cylindrical component 60 in a collapsed position against the biasing force of the spring 54. Also, the spring 54 is compressed between the needle hub 22 and the flip cap 90. The flip cap 90 that rests inside the end of the first cylindrical component 60 compresses the spring 54. The needle 24 extends from the needle hub 22 through the spring 54, through the flip cap 90, and exits the needle shield assembly 20 through the hole 51 in the end of the first cylindrical component 60. The twist cap 90 is twisted so that the needle 24 passes through the twist cap hole 48.

A user places the needle 24 under the skin and then depresses the actuation pads 74 that pivot the latches 38 releasing the first cylindrical component 60. The compressed spring 54 expands pushing the flip cap 90 and first cylindrical component 60 in a direction along the needle 24. The first and second cylindrical components 60, 70 move until they hit the stops within the second and third cylindrical components 70, 80 respectively. Once the expanding cylindrical components stop moving, the first cylindrical component 60 has extended beyond the end 68 of the needle 24, and the needle 24 is then completely enclosed within the needle shield assembly 20. Once the spring 54 has moved the flip cap 90 beyond the end 68 of the needle 24, the flip cap 90 twists so that its axis is in greater alignment with an axis of the needle shield assembly 20, and the flip cap hole 48 is not aligned with the hole 51 in the first cylindrical component 60. In this position, the flip cap 90 blocks the hole 51 in the end of the first cylindrical component 60, and thus prevents the end 68 of the needle 24 from exiting the needle shield assembly 20 again. Therefore, unintended needlesticks with a used needle are prevented.

The components described thus far are common to many of the unique variations possible within the scope of the current invention. Other variations of the closing structure and first cylindrical components may also be adapted to the present invention. The following descriptions describe the other embodiments of the present invention. Because the closing structure for each of the versions presented and the first cylindrical component are dependent on common design features and are designed to function together in a specific way, the closing structure and the cylindrical distal components will be described for each of the embodiments of the present invention.

Figure 32:
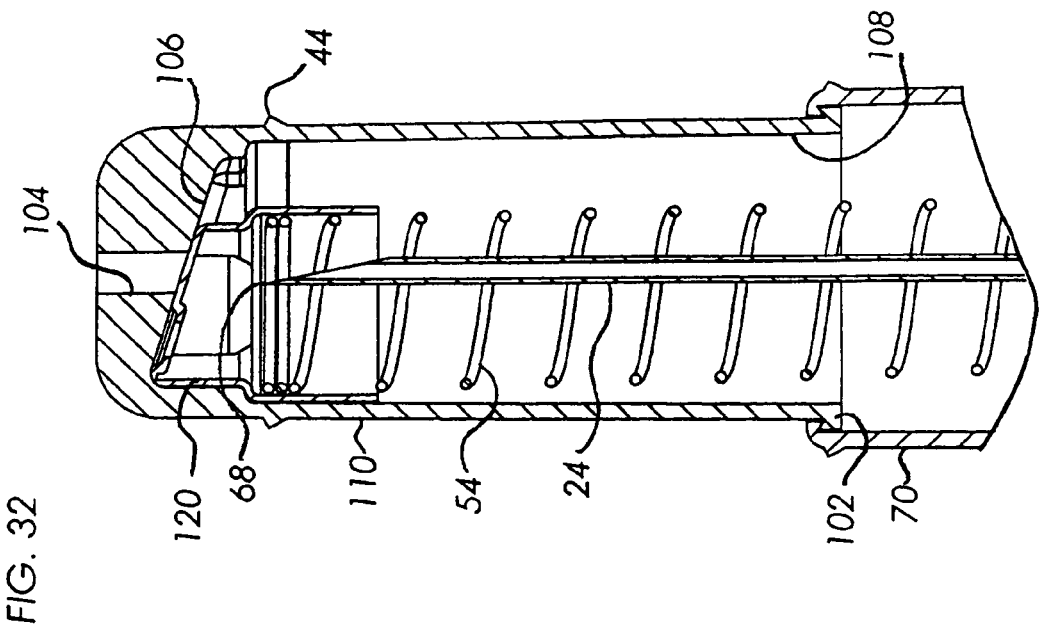
FIG. 32 shows an enlarged partial side elevation view of an exemplary safety needle of the slide cap version with the shield deployed.
Figure 31:
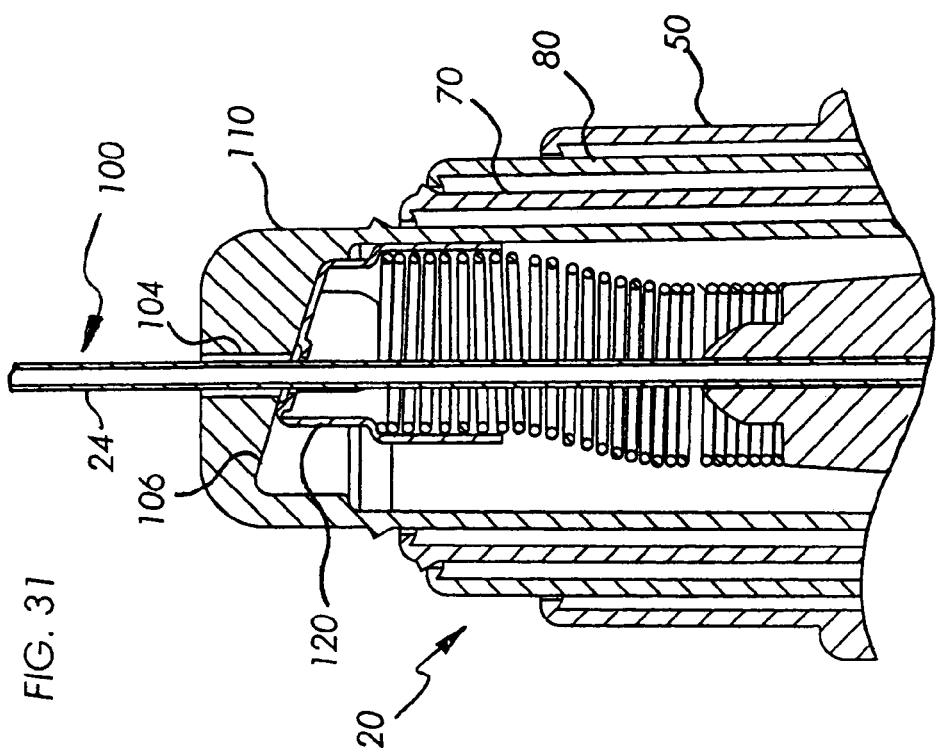
FIG. 31 shows an enlarged partial side elevation view of an exemplary safety needle of the slide cap version with the shield un-deployed.
Figure 37:
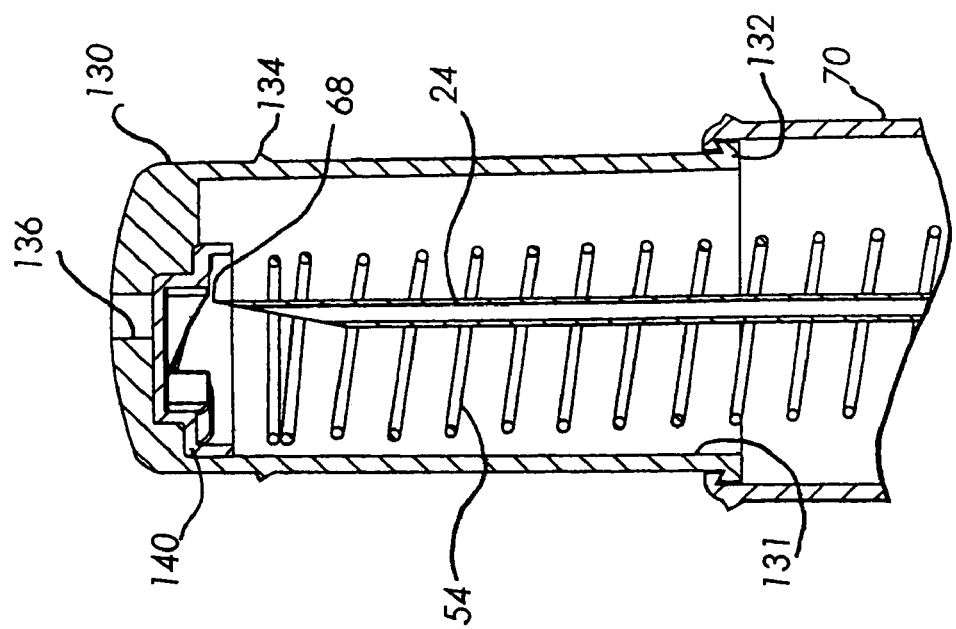
FIG. 37 shows an enlarged partial side elevation view of an exemplary safety needle of the twist cap version with the shield deployed.

FIGS. 31 and 32 show an embodiment of the present invention with a slide cap 120 within a firsts cylindrical component 110. The first cylindrical component 110 has a substantially rigid elongated tubular structure having a proximal and a distal end and having an opening 104 aligned with the axis of the actuation component 40 extending continuously between the proximal and the closed distal end. The first cylindrical component 110 includes an annular structure 102 used as a retaining ring, wherein the annular structure being on the most proximal end of the outer surface of the component 110 so as to prevent the component 110 from advancing past second cylindrical component 70. Thus the first cylindrical component 110 and the second cylindrical component 70 form collaspible interlocking members.

The slide cap 120 is located within the first cylindrical component 110. The first cylindrical component 110 includes an annular ring 44 positioned on the distal outer surface of the first cylindrical component 110 so as to prevent the second cyhndrical component 70 from advancing past the first cylindrical component 110. The distal end of the first cylindrical component 110 has an annular opening 104 in the most distal part of the first cylindrical component 110 and having its axis in alignment with the axis of the first component so as to allow the needle cannula 24 to pass through it. Yet another feature of the first cylindrical component 110 is a surface 106 positioned at the most distal end of an internal opening 108 and the surface 106 is slanted at an angle to the axis of the first cylindrical component 110. FIG. 35 shows the first cylindrical component 110 having a recessed area consisting of two parallel walls 111 being spaced apart so as to allow surfaces 124 of cap 120 (FIG. 33) to be in a sliding fit between the walls 111, and the walls are oriented in the slanted direction of surface 106.

FIGS. 33–34 show the slide cap component 120 as a substantially rigid elongated tubular structure having a proximal and a distal end and having an opening aligned with the axis of the actuation component 40 extending continuously between the proximal and the closed distal end of the cap. The most distal outer surface 122 of the slide cap 120 is slanted at an angle to the axis of the slide cap 120. The surface is at an angle matching the interior surface 106 of the first cylindrical component 110 of the slide cap version. The slide cap 120 has an annular opening 112 on the slanted surface 122, offset and a distance from the center axis of slide cap 120. The slide cap 120 has a recessed annular area 116 centered around annular opening 112 and protruding toward the proximal opening of the slide cap 120 and forming a raised surface 116a around the annular opening on the underside of slanted surface 122. A purpose of raised surface 116a is to prevent the needlepoint 68 from sliding into annular opening 112. The slide cap 120 has a larger tubular section 118 extending proximally a given distance and its distal end merging with the smaller tubular section 119, forming a recessed 121 area for the spring 54 to nest into. The tubular section 119 fanns a barrier around the needlepoint 68 for added protection. As shown in FIG. 33, the parallel walls 124 are equally spaced from the centerline of slide cap 120.

The operation of the slide cap 120 embodiment of the present invention will now be described. As shown in FIG. 31, the needle shield assembly 20 is attached to a syringe. The needle shield assembly 20 is in a compressed state with the first, second, and third cylindrical components 110, 70, 80 collapsed and nested within each other. The latch 38 (not shown) engages the first cylindrical component 110 and holds the first cylindrical component 110 in a collapsed position against the biasing force of the spring 54. Also, the spring 54 is compressed between the needle hub 22 and the slide cap 120. The slide cap 120 that rests inside the end of the first cylindrical component 110 compresses the spring 54. The needle 24 extends from the needle hub 22 through the spring 54, through the slide cap 120, and exits the needle shield assembly 20 through the hole 104 in the end of the first cylindrical component 110. The slide cap 120 is aligned so that the needle 24 passes through the slide cap hole 112.

A user places the needle 24 under the skin and then depresses the actuation pads 74 that pivot the latches 38 releasing the first cylindrical component 110. The compressed spring 54 expands pushing the slide cap 120 and first cylindrical component 110 in a direction along the needle 24. The first and second cylindrical components 110, 70 move until they hit the stops within the second and third cylindrical components 70, 80 respectively. Once the expanding cylindrical components stop moving, the first cylindrical component 110 has extended beyond the end 68 of the needle 24, and the needle 24 is then completely enclosed within the needle shield assembly 20. Once the spring 54 has moved the slide cap 120 beyond the end 68 of the needle 24, the slide cap 110 slides along the slanted inner surface 106, so that the slide cap hole 112 is not aligned with the hole 104 in the first cylindrical component 110. In this position, the slide cap 120 blocks the hole 104 in the end of the first cylindrical component 110, and thus prevents the end 68 of the needle 24 from exiting the needle shield assembly 20 again. Therefore, unintended needlesticks with a used needle are prevented.

FIGS. 36–39 show an embodiment of the present invention with a twist cap closing structure. The first cylindrical component 130 is a substantially rigid elongated tubular structure having a proximal and a distal end and having an opening 131 aligned with the axis of actuation component 50 extending continuously between the proximal and the closed distal end of the first cylindrical component 130. The first cylindrical component 130 has an annular structure 132 used as a retaining ring, where the annular structure being on the most proximal end of the outer surface of the first component 130 so as to prevent the first cylindrical component 130 from advancing past the second cylindrical component 70.

The first cylindrical component of the twist cap 140 embodiment has an annular ring 134 positioned on the distal outer surface of first cylindrical component 130 so as to prevent the second cylindrical component 70 from advancing past the first cylindrical component 130. The first cylindrical component has an annular opening 136 in the most distal part of the first component and has its axis in alignment with the axis of the first component so as to allow the needle cannula 24 to pass through it. The first cylindrical component of the twist cap embodiment may have three ramping surfaces 138 arranged in a circular fashion and equally spaced around a circle. The circular pattern of ramping surfaces 138 has its axis parallel to and offset from the axis of first most distal component 130. The ramping surfaces 138 ramp in a proximal to a distal direction.

Figure 41:
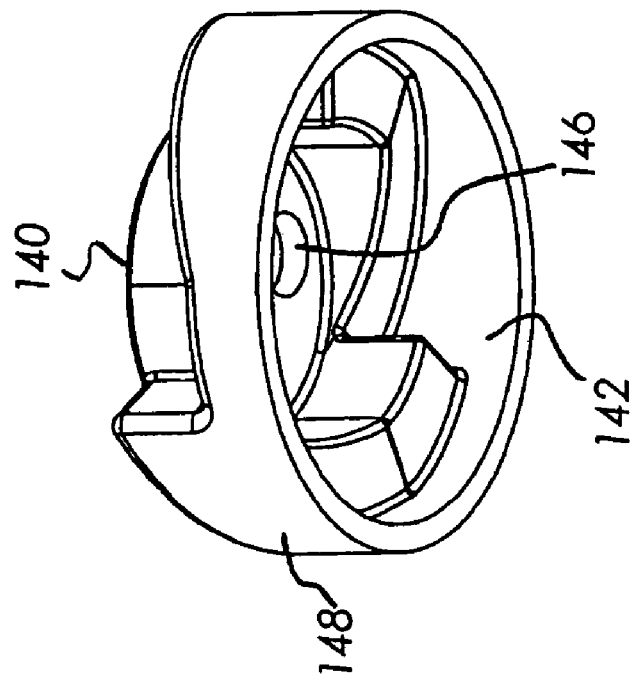
FIG. 41 shows an enlarged bottom isometric view of an exemplary twist cap.
Figure 40:
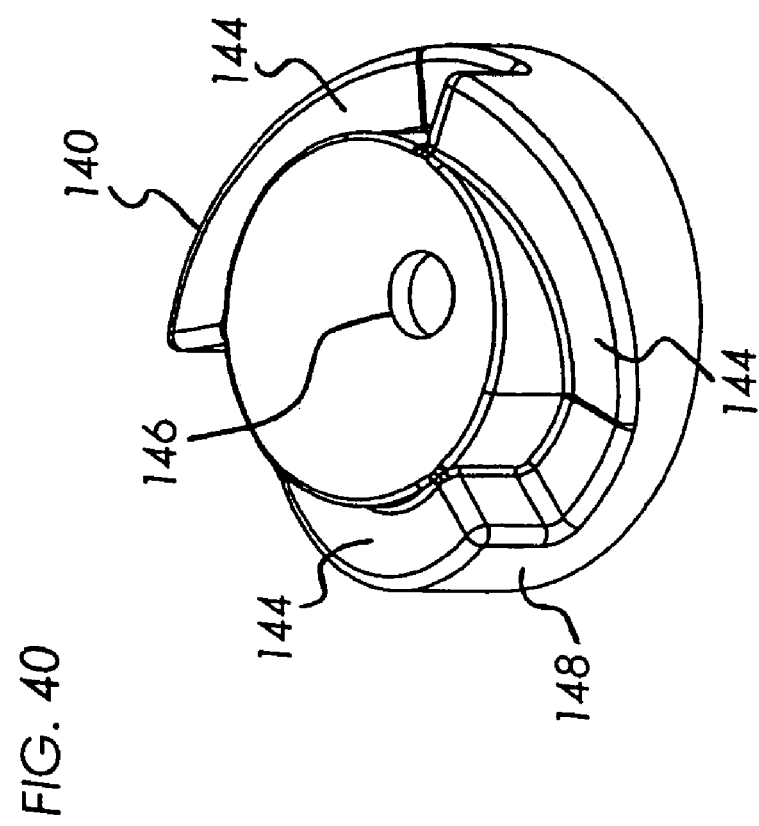
FIG. 40 shows an enlarged top isometric view of an exemplary twist cap.

FIGS. 40–41 show the twist cap component 140. The twist cap 140 is a substantially rigid elongated tubular structure having a proximal and a distal end and having an opening 142 aligned with the axis of the actuation component 50, wherein the opening 142 extends continuously between the proximal and the closed distal end of the cap. The twist cap 140 may have distal surfaces with three ramping surfaces 144 arranged in a circular fashion and equally spaced around the circle. The circular pattern of the ramping surfaces 144 matches the interior ramping surfaces 138 of the first cylindrical component 130. The ramping surfaces 144 ramp in a proximal to a distal direction. The twist cap 140 also has an annular opening 146 on the most distal surface of the cap 140 with its axis parallel to and offset from the axis of the cap 140. The cap 140 has a recessed annular area (not shown) similar to the slide cap version as 116. The annular area is centered around the annular opening 146 and protrudes toward the internal opening 142 of the cap 140, forming a raised surface around the annular opening 146 on the proximal side of the most distal surface. A purpose of the raised surface is, to prevent the needlepoint 68 from sliding into the annular opening 146. The cap has a larger tubular section 148 extending proximally and having a distal end connected to the smaller tubular section forming a recessed area 142 for the spring 54 to nest into. Another purpose of the tubular section 148 is to form a barrier around needlepoint 68 for added protection.

Figure 36:
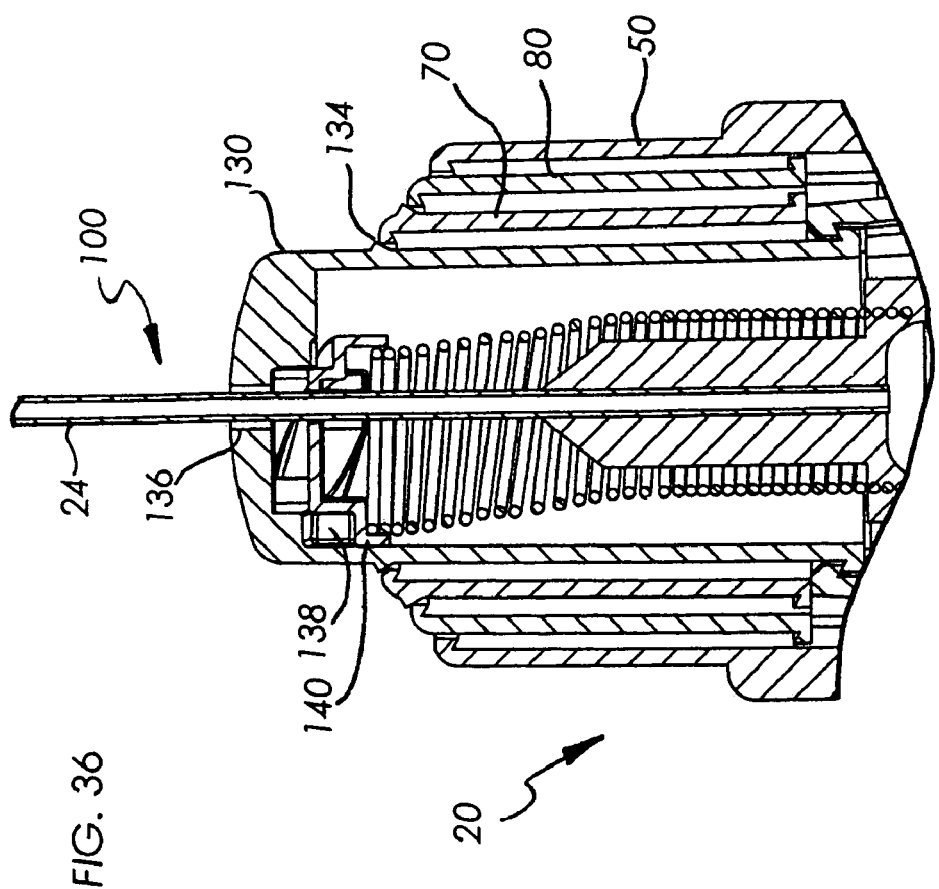
FIG. 36 shows an enlarged partial side elevation view of an exemplary safety needle of the twist cap version with the shield un-deployed
Figure 39:
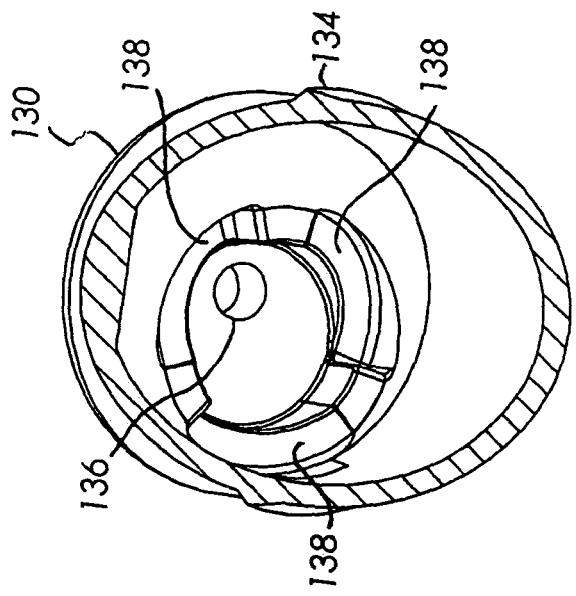
FIG. 39 shows an enlarged cut away isometric view of an exemplary first cylindrical component of the twist cap version showing the cam surfaces.
Figure 38:
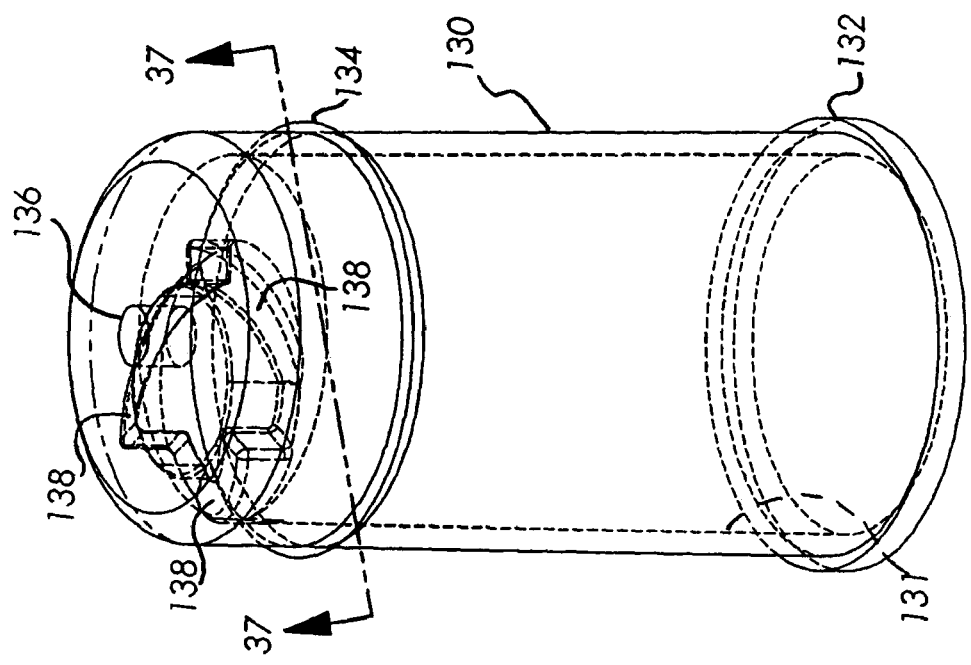
FIG. 38 shows an enlarged top isometric view of an exemplary first cylindrical component of the twist cap version.

The operation of the twist cap 140 embodiment of the present invention will now be described. As shown in FIG. 36, the needle shield assembly 20 is attached to a syringe. The needle shield assembly 20 is in a compressed state with the first, second, and third cylindrical components 130, 70, 80 collapsed and nested within each other. The latch 38 (not shown) engages the first cylindrical component 130 and holds the first cylindrical component 130 in a collapsed position against the biasing force of the spring 54. Also, the spring 54 is compressed between the needle hub 22 and the twist cap 140. The twist cap 140 that rests inside the end of the first cylindrical component 130 compresses the spring 54. The needle 24 extends from the needle hub 22 through the spring 54, through the twist cap 140, and exits the needle shield assembly 20 through the hole 136 in the end of the first cylindrical component 130. The twist cap 140 is aligned so that the needle 24 passes through the twist cap hole 146. In this position the top of the twist cap ramps 144 engage the top of the ramps 138 on the first cylindrical component 130. In this position the twist cap hole 146 aligns with the hole 136 in the end of the first cylindrical component 130.

A user places the needle 24 under the skin and then depresses the actuation pads 74 that pivot the latches 38 releasing the first cylindrical component 130. The compressed spring 54 expands pushing the twist cap 140 and first cylindrical component 130 in a direction along the needle 24. The first and second cylindrical components 130, 70 move until they hit the stops within the second and third cylindrical components 70, 80 respectively. Once the expanding cylindrical components stop moving, the first cylindrical component 130 has extended beyond the end 68 of the needle 24, and the needle 24 is then completely enclosed within the needle shield assembly 20. Once the spring 54 has moved the slide cap 140 beyond the end 68 of the needle 24, the ramps 144 on the twist cap 140 slide and twist along the ramps 138 in the first cylindrical component 130. In this position, the twist cap 140 blocks the hole 136 in the end of the first cylindrical component 130, and thus prevents the end 68 of the needle 24 from exiting the needle shield assembly 20 again. Therefore, unintended needlesticks with a used needle are prevented.

FIGS. 42–45 show an embodiment of the present invention using overlapping disks 160. The first cylindrical component 150 of this embodiment has a substantially rigid elongated tubular structure with a proximal and a distal end and with an opening 152 aligned with the axis of the actuation component 50 and extending continuously between the proximal and the closed distal end of the first cylindrical component. The first cylindrical component has an annular structure 154 used as a retaining ring and has an annular structure 154 on the most proximal end of the outer surface of component 150 so as to prevent the first cylindrical component 150 from advancing past the second cylindrical component 70.

The first cylindrical component 150 has an annular ring 156 positioned on the distal outer surface of the first cylindrical component 150 so as to prevent the second cylindrical component 70 from advancing past the first cylindrical component 150. The first cylindrical component 150 has an annular opening 158 at the most distal part of the first component 150 and has its axis in alignment with the axis of the cylindrical first component 150 so as to allow needle cannula 24 to pass through it. The first cylindrical component 150 has a pocket 159 for accommodating overlapping disks 180, 184 and activation spring 170. The pocket 159 is positioned at the most distal end of the internal opening and has its axis parallel to and offset from the axis of the first cylindrical component 150. The pocket 159 has sufficient depth so as to contain the spring 170 connected to the 180, 184 double disks 160 and has a length sufficient to allow the spring 170 to bias the two disks 160 until the openings 162 and 164 in the disks are no longer in alignment.

Figure 47:
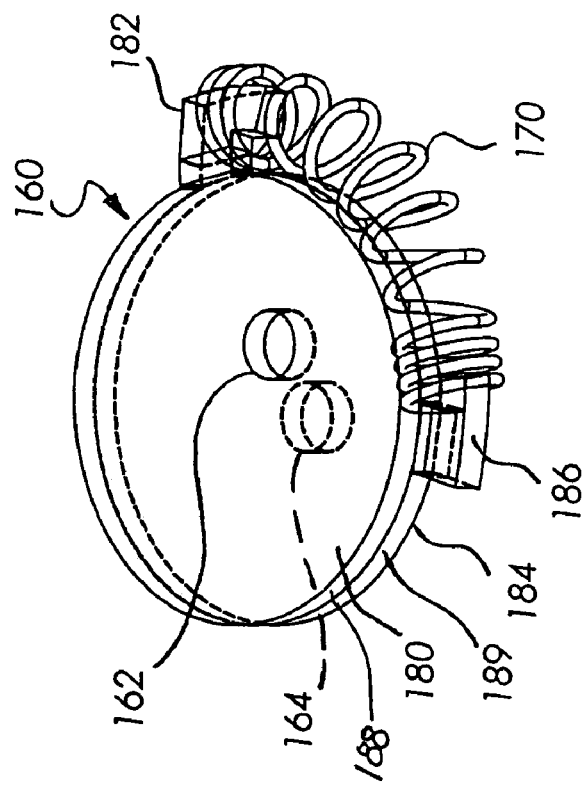
FIG. 47 shows an enlarged top isometric view of an exemplary overlapping disks version deployed.
Figure 46:
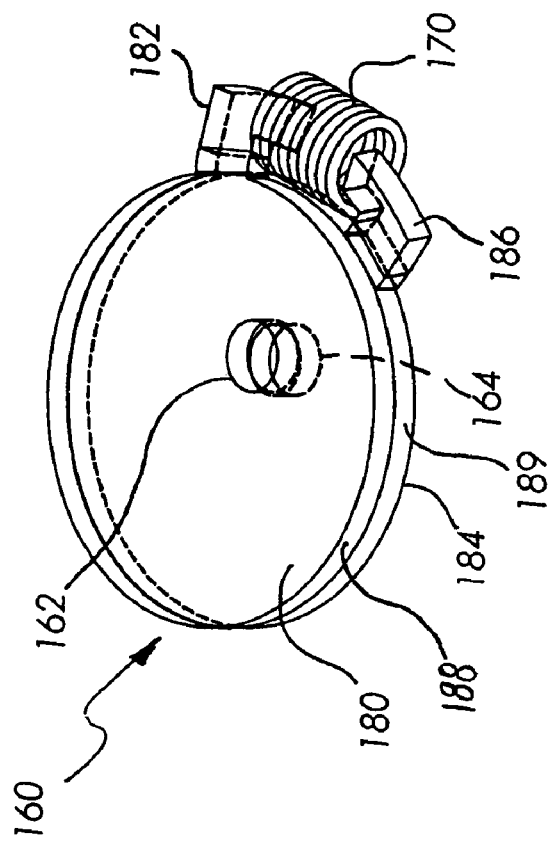
FIG. 46 shows an enlarged view of an exemplary overlapping disks version un-deployed.
Figure 52:
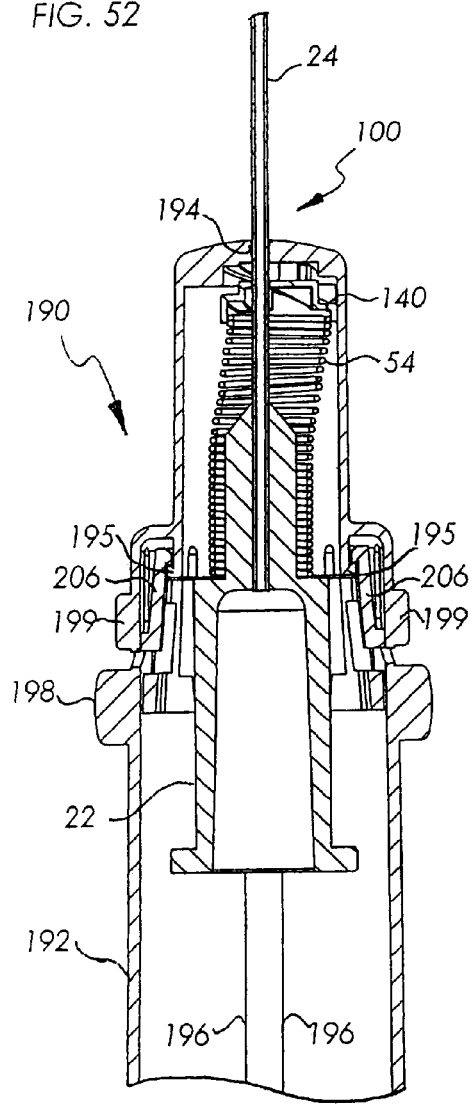
FIG. 52 shows an enlarged partial cross sectional side elevation view of an exemplary one-cap version un-deployed.

FIGS. 46 and 47 show the overlapping disk components 160 including two metallic discs 180 and 184 that may alternatively be made of hard plastic. The disks 180, 184 have a proximal and a distal surface being parallel to each other. The disks 180, 184 have a hook shaped member 182, 186 protruding out from the edge a given distance, and the hook member 182, 186 faces in a clockwise direction on disk 180, and in a counter clockwise direction on disk 184. The disks 182, 186 have an annular opening 162 and 164 respectively with their axis parallel to the axis of a cylindrical part 188 and 189 of the disks 180 and 184 respectively and offset from the axis. The openings 188 and 189 of disks 180 and 184 are aligned so as to share a common axis when the two hooks 182 and 186 are closest to each other so as to allow the needle cannula 24 to pass through them. When the two hooks 182 and 186 are the farthest from each other, the two openings 162 and 164 do not overlap and therefore, the needle 24 is prevented from advancing past overlapping disks 180 and 184.

The overlapping disks embodiment has a spring 170 with the spring 170 having its axis substantially perpendicular to the axis of the disks 180, 184 and having its proximal end engaged in the hook 186 of disk 184 and its distal end engaged in the hook 182 of disk 180 so as to bias the disks 180, 184 into rotation in opposite directions and cause the openings 162 and 164 in the disks to become misaligned so as to prevent the passage of needlepoint 68.

Figures 42, 43:
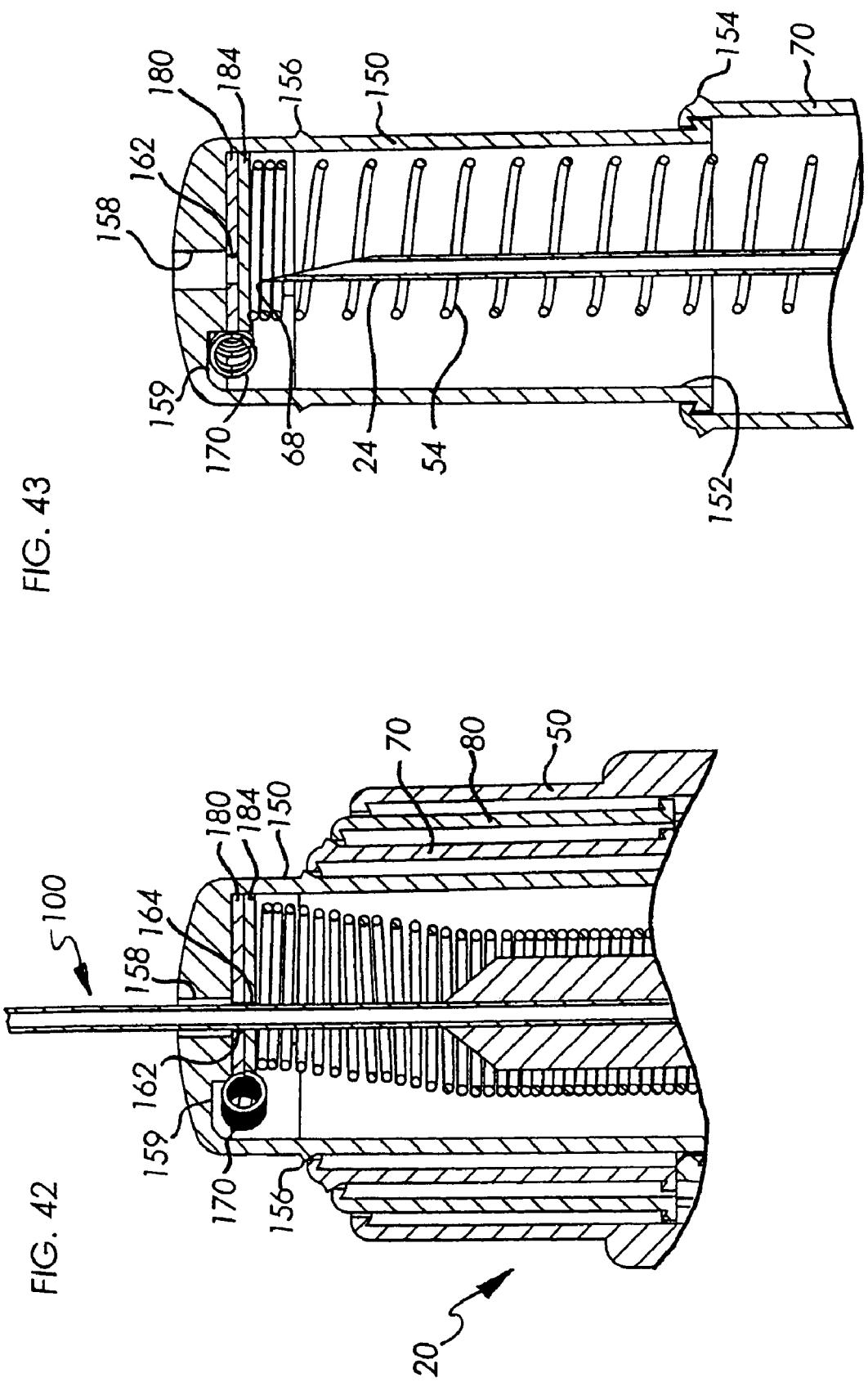
FIG. 42 shows an enlarged partial side elevation view of an exemplary safety needle of the overlapping disks version with the shield un-deployed.
FIG. 43 shows an enlarged partial side elevation view of an exemplary safety needle of the overlapping disks version with the shield deployed.
Figure 45:
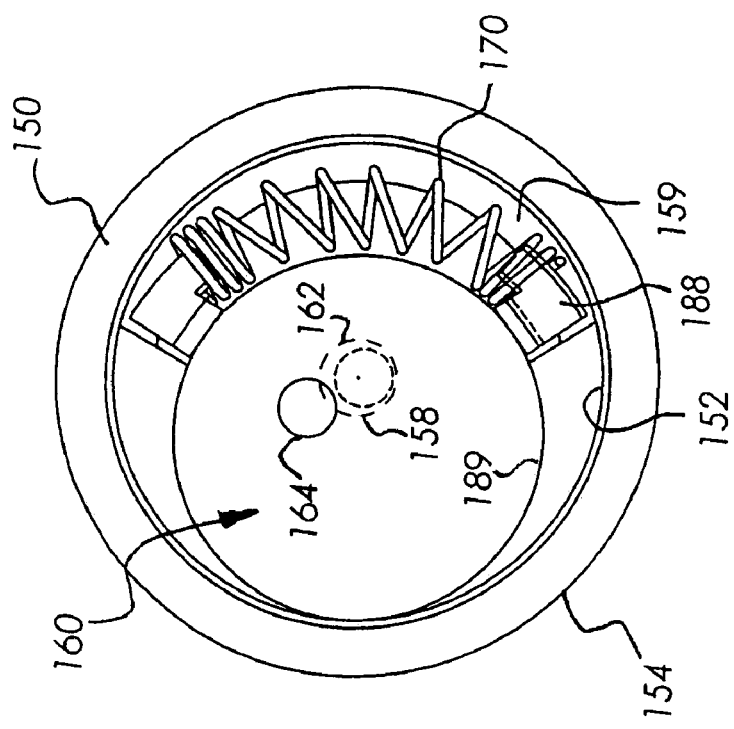
FIG. 45 shows an enlarged bottom view of an exemplary overlapping disks version deployed.
Figure 44:
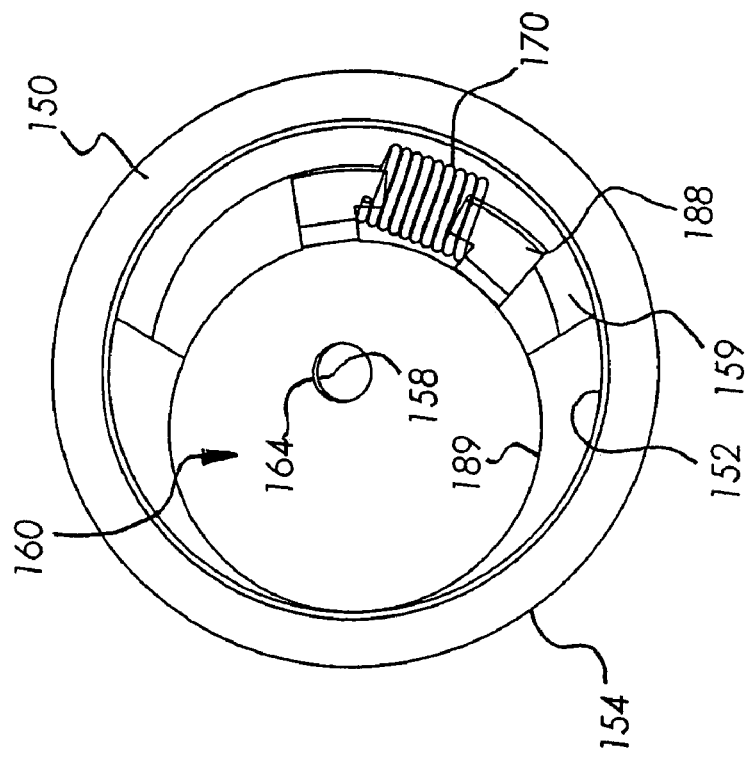
FIG. 44 shows an enlarged bottom view of an exemplary overlapping disks version un-deployed.

The operation of the overlapping disks 160 embodiment of the present invention will now be described. As shown in FIG. 42, the needle shield assembly 20 is attached to a syringe. The needle shield assembly 20 is in a compressed state with the first, second, and third cylindrical components 150, 70, 80 collapsed and nested within each other. The latch 38 (not shown) engages the first cylindrical component 150 and holds the first cylindrical component 150 in a collapsed position against the biasing force of the spring 54. Also, the spring 54 is compressed between the needle hub 22 and the overlapping disks 160. The overlapping disks 160 that rest inside the end of the first cylindrical component 150 compress the spring 54. The needle 24 extends from the needle hub 22 through the spring 54, through the overlapping disks 160, and exits the needle shield assembly 20 through the hole 158 in the end of the first cylindrical component 150. The overlapping disks 160 are aligned so that the needle 24 passes through the overlapping disk holes 162, 164.

A user places the needle 24 under the skin and then depresses the actuation pads 74 that pivot the latches 38 releasing the first cylindrical component 150. The compressed spring 54 expands pushing the overlapping disks 160 and first cylindrical component 150 in a direction along the needle 24. The first and second cylindrical components 150, 70 move until they hit the stops within the second and third cylindrical components 70, 80 respectively. Once the expanding cylindrical components stop moving, the first cylindrical component 150 has extended beyond the end 68 of the needle 24, and the needle 24 is then completely enclosed within the needle shield assembly 20. Once the spring 54 has moved the slide cap 160 beyond the end 68 of the needle 24, the spring 170 causes the overlapping disks 160 to rotate causing the overlapping disk holes 162 and 164 to become unaligned, and thus prevents the end 68 of the needle 24 from exiting the needle shield assembly 20 again. Therefore, unintended needlesticks with a used needle are prevented.

FIGS. 48–53 show another embodiment of the present invention using a single shield 190. The single shield embodiment has a single cap component 192 being a substantially rigid elongated tubular structure having a proximal and a distal end and having an opening 194 aligned with the axis of a release ring 200 with the tubular structure extending continuously between the proximal and the closed distal end of single cap 190. The cap has a most distal inner surface with an opening 194 and surfaces as previously described for, alternatively, the flip cap 90, the slide cap 120, the twist cap 140 and the overlapping disks 160, each having the appropriate matching geometry within the single caps 190 as shown, for example, in FIGS. 50–51 with the twist cap 140 version.

The single cap component 192 may have two retaining open slots 196 on either side of the tubular segment 197 of the component 192 with the slots 192 in parallel alignment to the axis of the component 192, diametrically opposed and forming an opening in the walls of tubular segment 197. In addition the proximal end of slots 196 begin in a position so as to serve as a stop when contacted by tabs 202 on the release ring 200 when the single shield 190 is deployed and preventing the single shield 190 from advancing past release ring 200. The single shield 190 may have an annular structure 198 positioned at a distance from the distal end and on the outer surface of the single shield and being sized so as to allow the protective cap 10 to snap on to the annular structure 198. The single shield component 180 also has a tubular structure 193 extending proximally a distance from the inner surface of single shield 190. The single shield component 190 has an annular retaining ring 195 at the most proximal end of tubular structure 193 on the outer surface of the tubular structure. The single shield component 190 also has finger actuated pads 199 positioned diametrically opposed and in alignment with heel features 204 of the release ring 200, and a keying tab may also be implemented to align the actuation pads 199 with the heels 204 of release ring 200. When pressed, the pads 199 apply pressure on the heels 204 of latches 206 so as to displace the latches 208 in release ring 200 causing the latches 208 in the release ring 200 to pivot and release the single shield component 190 thereby deploying the single shield 190. The single shield component 190 also has an annular opening 194 in the most distal part with its axis in alignment with the axis of the single shield 190 so as to allow the needle cannula 24 to pass through it.

Figure 53:
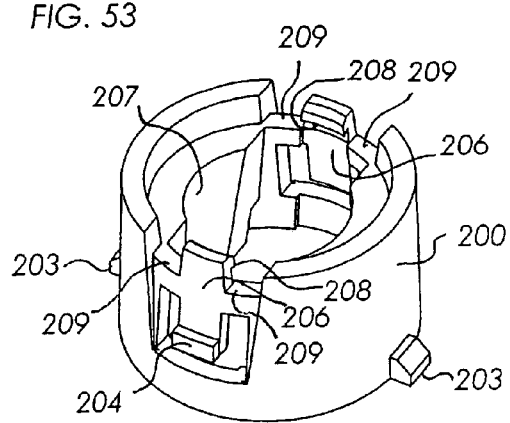
FIG. 53 shows an enlarged top isometric view of an exemplary release ring of the one cap version.
Figure 54:
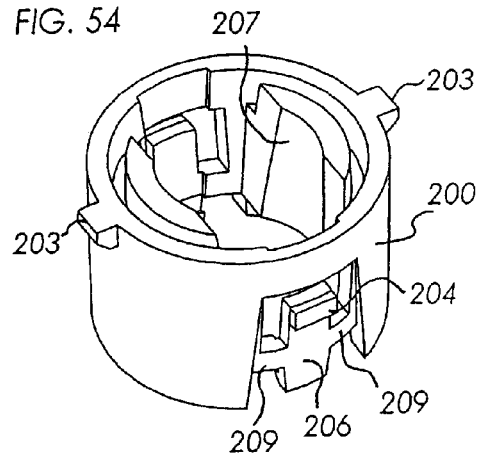
FIG. 54 shows an enlarged bottom isometric view of an exemplary release ring of the one cap version.
Figure 57:
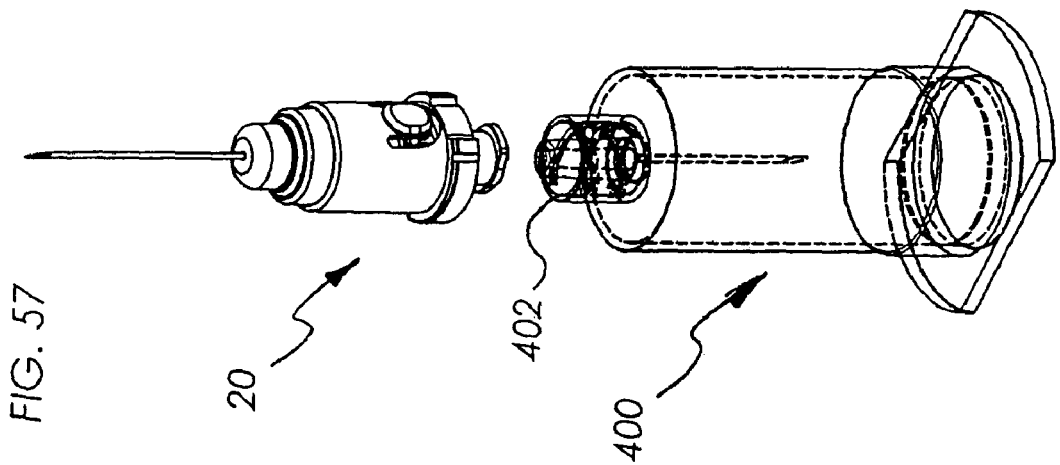
FIG. 57 shows an enlarged top isometric view of an exemplary safety needle of the present invention in use with a blood collection device.

The release ring 200 shown in FIGS. 53–54 is a substantially rigid elongated structure having a proximal and a distal end and having an opening aligned with the axis of the release ring 200 that extends continuously between the proximal and the distal ends. The opening in release ring 200 has an inner member 207 that rigidly connects with the hub of a cylindrical hypodermic needle. The release ring 200 also has two latches 206 diametrically opposed with a distal end having the hook portion 208 of the latch extending in the direction of the proximal end of the release ring 200. The hook feature 208 faces toward the axis of the release ring 200. The hook portion 208 of the latch 206 is engaged with the annular ring 195. The proximal part of the latch has a heel feature 204 with the heel facing away from the axis of the release ring 200. The latch 206 is pivotable and pivots when pressed upon with actuation pads 199 of the single shield component 190. The latch pivots 209 may be such that the pivots become disabled after actuation so as to prevent intentional rearming of hypodermic needle 24. The number of the latches 206 may be varied depending upon the size of the device and the end use application. The release ring 200 may have at least one tab 203 positioned at the proximal external surface of the release ring. The tab may engage the open slots 196 of the single shield 190 so as to slide freely the full length of the slot 196. When the single shield 190 is deployed and the spring 54 pushes the single shield 190 into a deployed position, the tabs 203 on the release ring 200 come to rest against the most proximal surface 194 of slots 196 in the single shield 190 thus preventing the single shield 190 from extending past the release ring 200.

Figure 58:
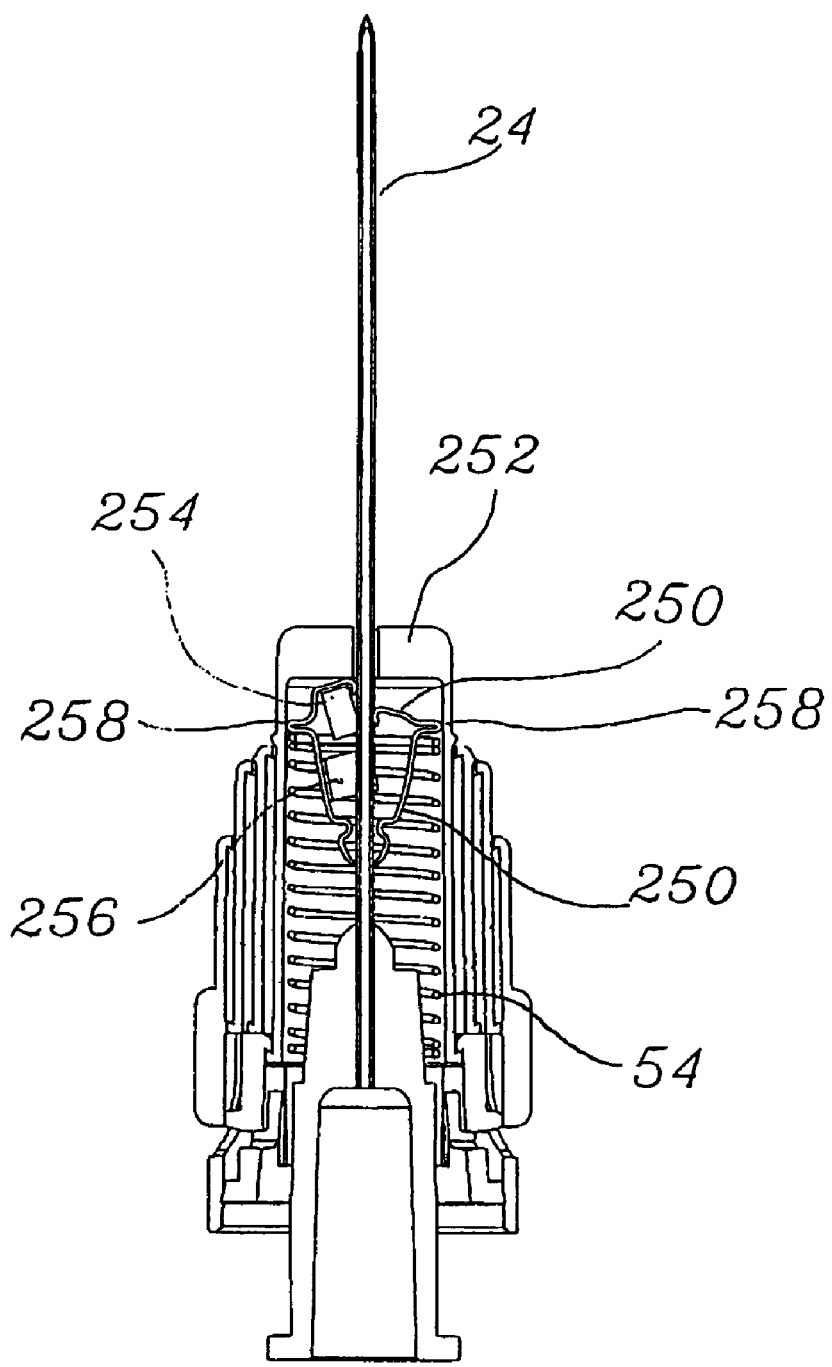
FIGS. 58–61 show an embodiment of the present invention with a clip closing structure.
Figure 59:
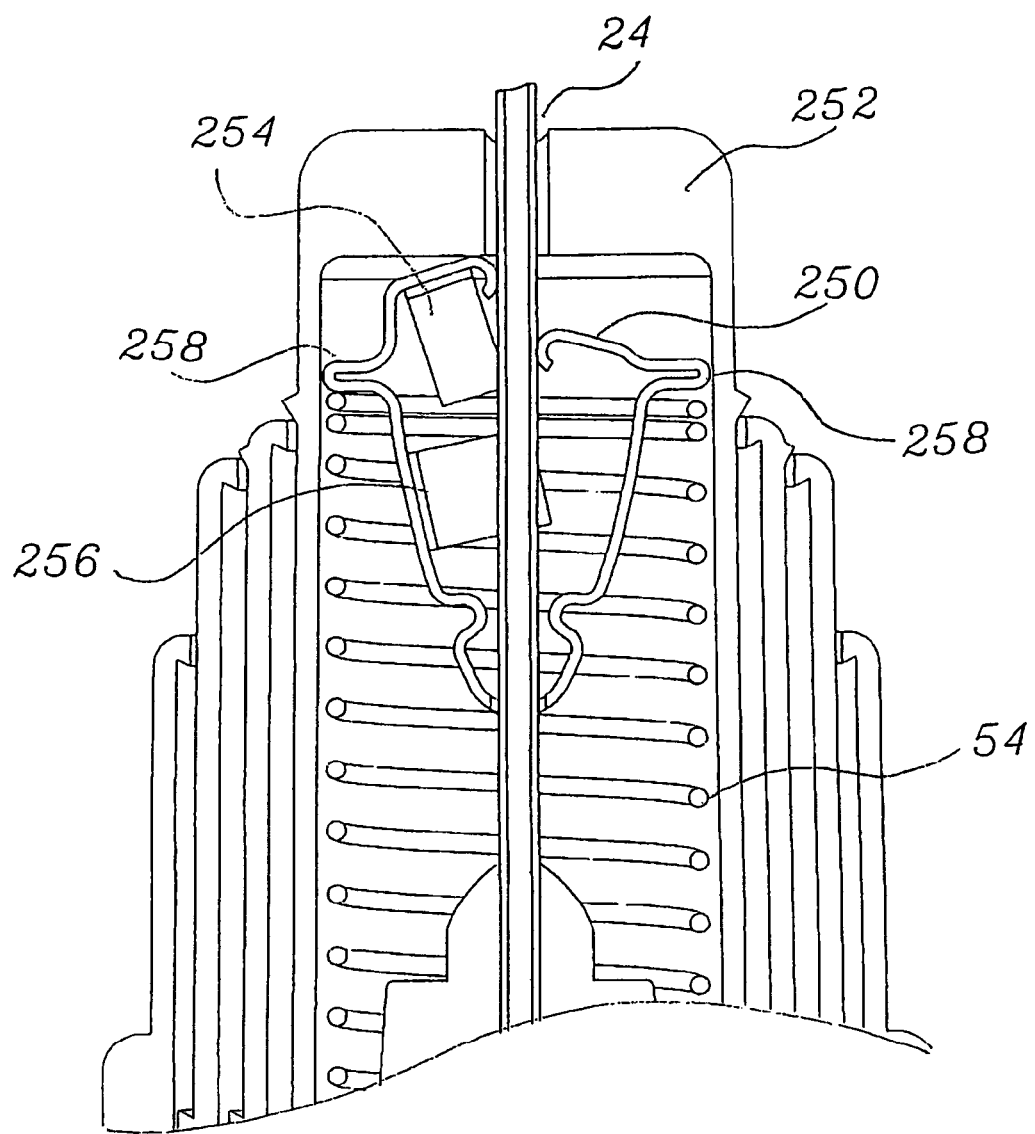
Figure 60:
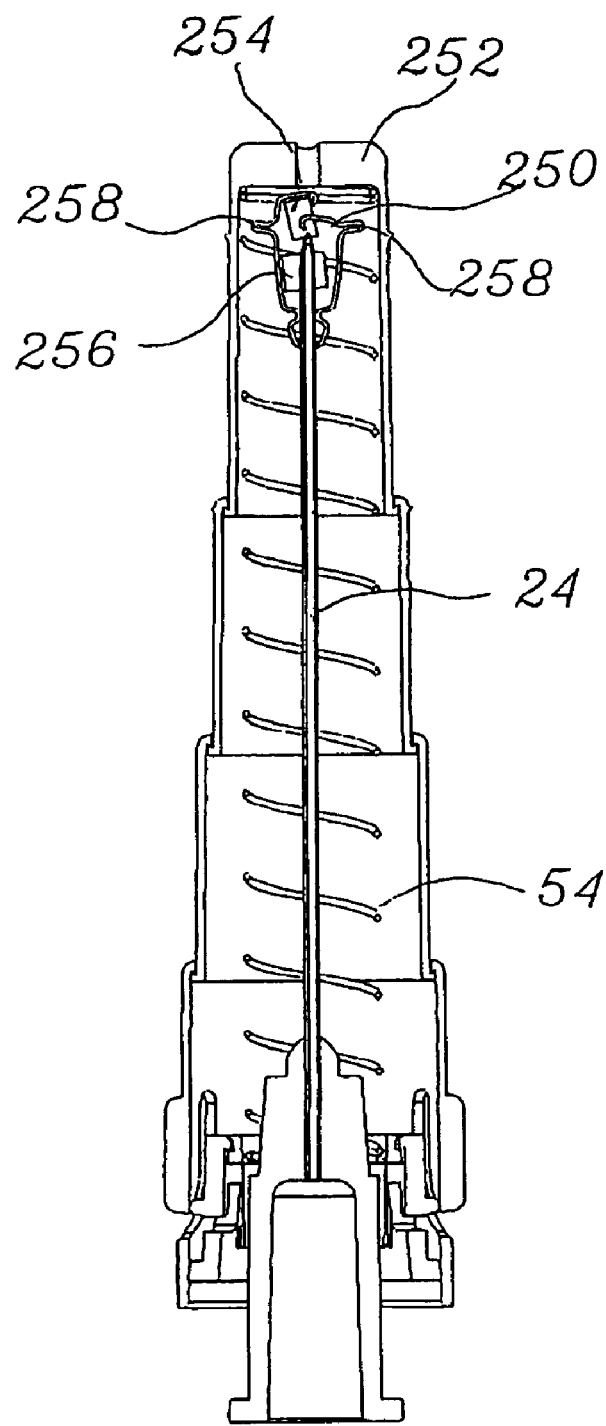
Figure 61:
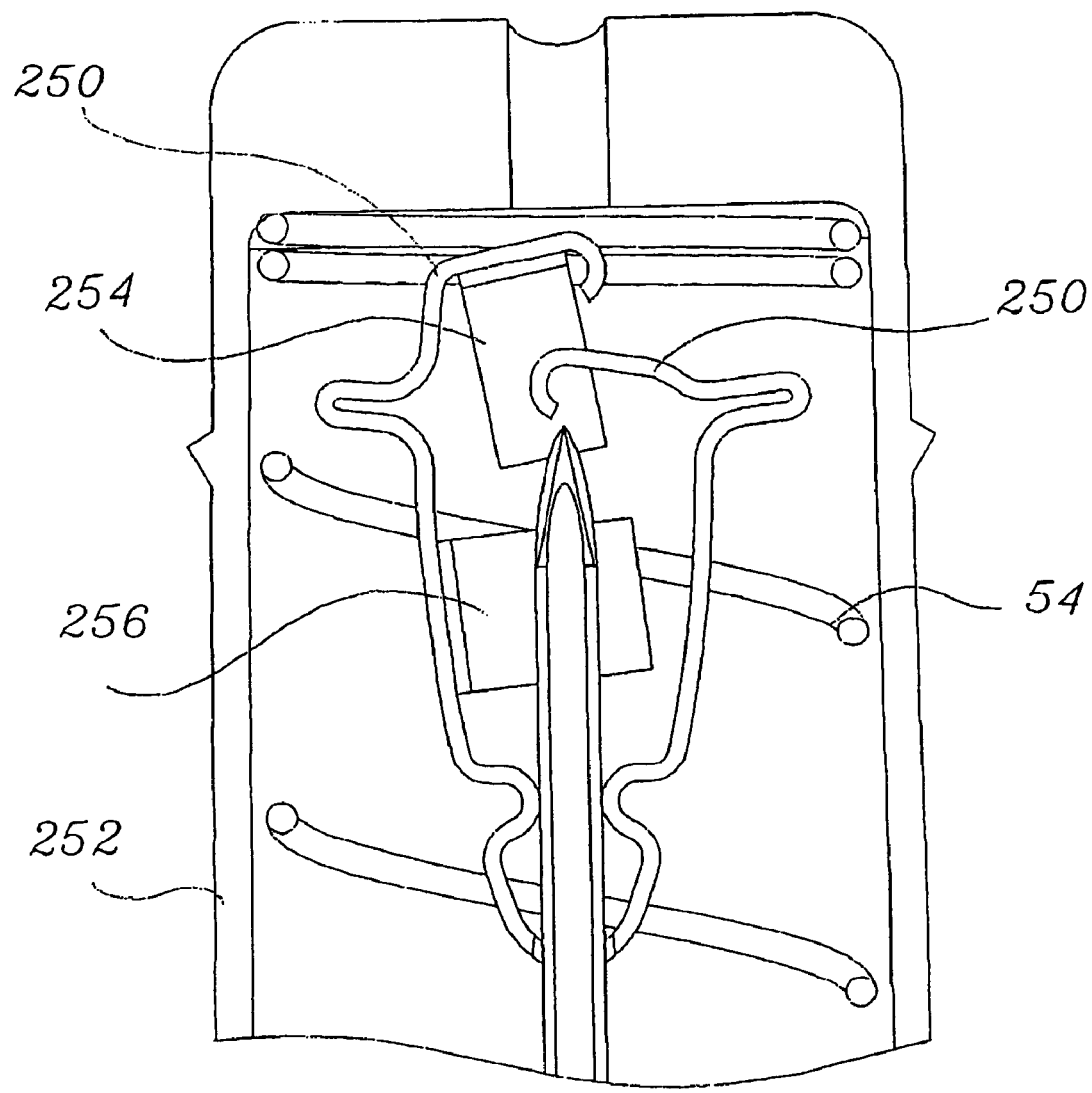

FIGS. 58–61 show an embodiment of the present invention with a clip closing structure. The first cylindrical component 252 is similar to those previously described. In FIG. 58 the needle shield assembly 20 is in a compressed state. The spring 54 is compressed between the needle hub 22 and a clip 250 near the end of the first cylindrical component 110. The needle 24 extends from the needle hub 22 through the spring 54, through the clip 250, and exits the needle shield assembly 20 through the hole 254 in the end of the first cylindrical component 252.

The clip 250 has two arms 256 through which the needle 24 passes. The two arms 256 press upon opposite sides of the needle 24 due to a spring action in the clip 250. The clip 250 also has two needle guards 258. The clip has two tabs 258 that are at the outer edges of the clip 250, and the spring 54 contacts the tabs 258 pressing the clip 250 away from the hub 22. The clip may be made of metal, plastic, or any other material that lends itself to a preferred manufacturing process.

The needle shield 20 using the clip 250 operates as follows. A user places the needle 24 under the skin and then depresses the actuation pads 74 that pivot the latches 38 releasing the first cylindrical component 150. The compressed spring 54 expands pushing the overlapping disks 160 and first cylindrical component 150 in a direction along the needle 24. Once the expanding cylindrical components stop moving, the first cylindrical component 150 has extended beyond the end 68 of the needle 24, and the needle 24 is then completely enclosed within the needle shield assembly 20. Once the spring 54 has moved the slide cap 160 beyond the end 68 of the needle 24, the two arms 256 move inward due to the spring force of the clip 250. The arms 256 block the needle, and thus prevents the end 68 of the needle 24 from exiting the needle shield assembly 20 again. The tabs 258 move inward allowing the spring 54 to pass the clip and continue pushing the first cylindrical component 252 out. In addition, the clip 250 as it closes grips the needle 24, preventing the clip from sliding off of the end of the needle. This allows the clip 250 to be used with needles of any length. Therefore, unintended needle-sticks with a used needle are prevented.

Figure 62:
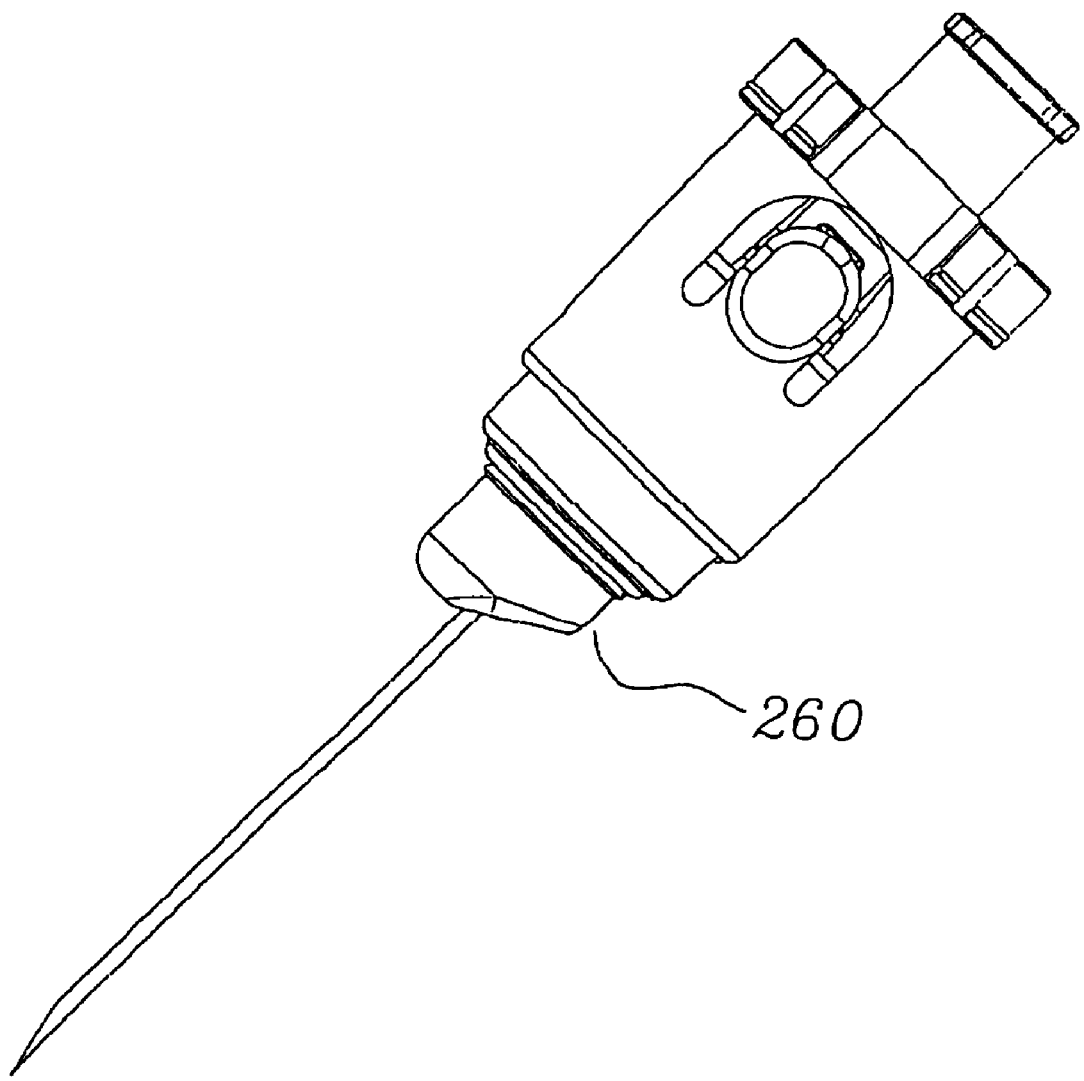
FIGS. 62 and 63 show another embodiment of the present invention with first cylindrical component at an angle with respect to the needle.
Figure 63:
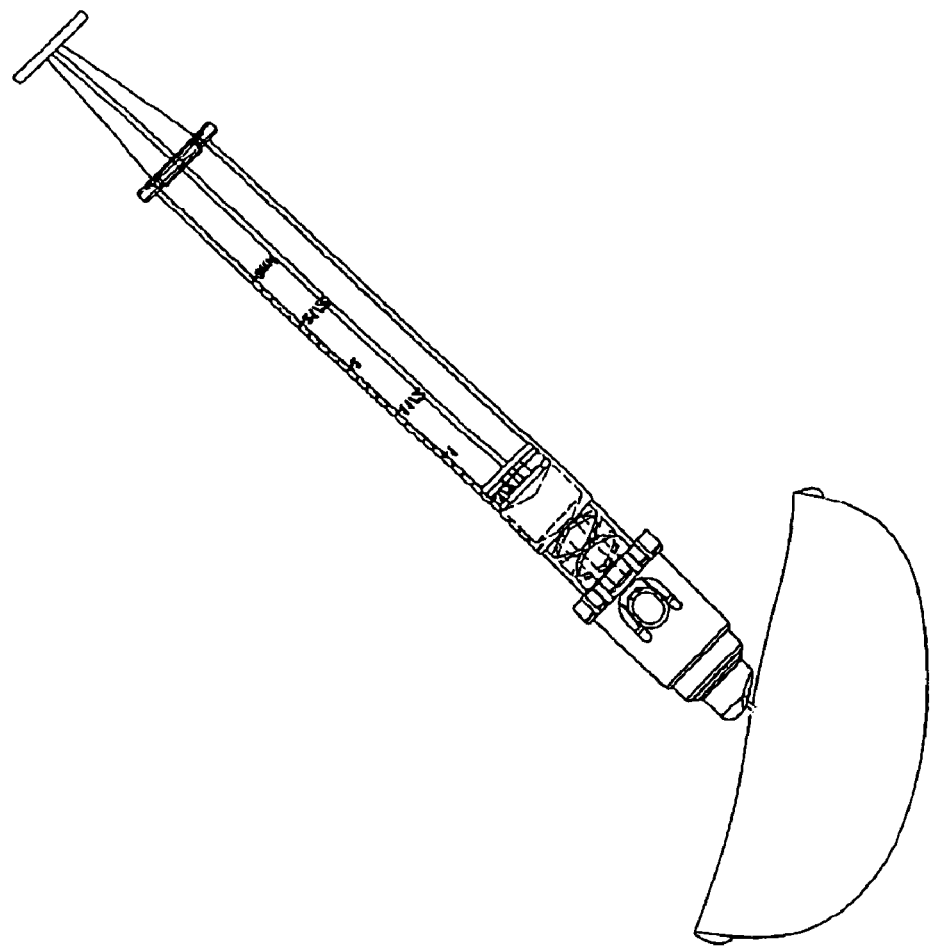

FIGS. 62 and 63 show another embodiment of the present invention. The end of the first cylindrical component 260 is at an angle with respect to the needle 24 to better align with the skin of the patient, rather then being perpendicular to the needle 24 as previously shown.

Figure 64:
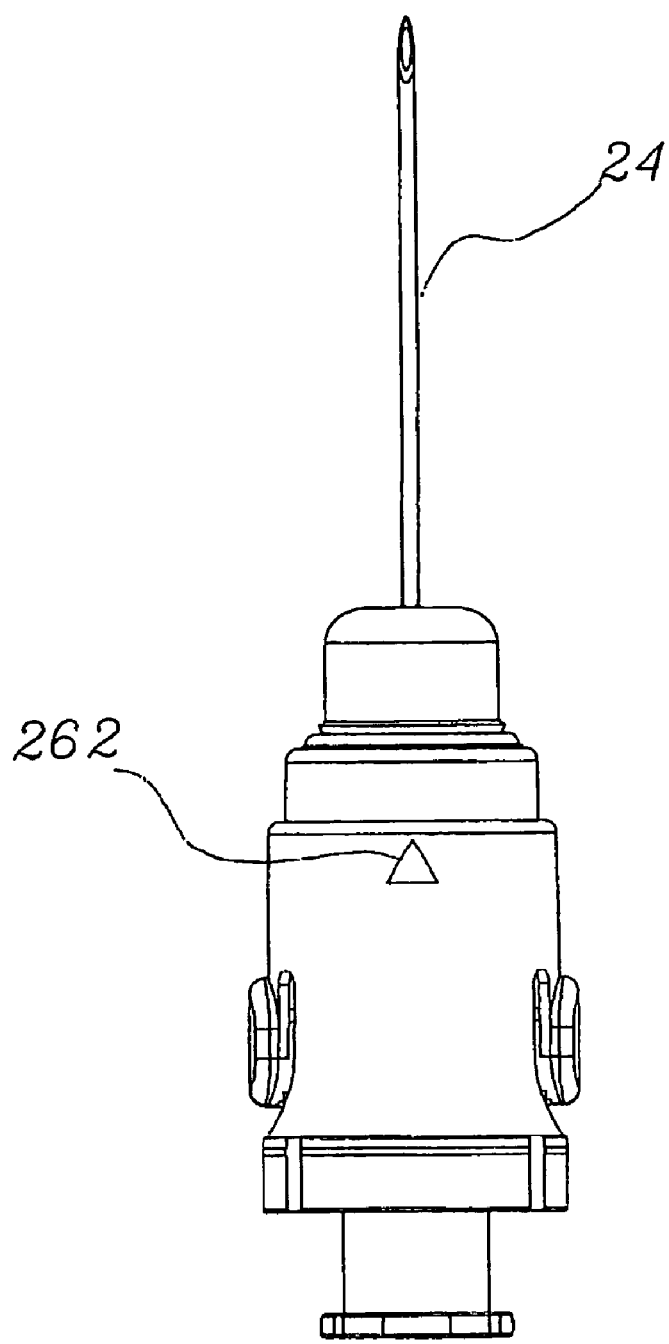
FIGS. 64 and 65 show another embodiment of the present invention with an identifying mark placed on the needle shield to show the orientation of the bevel on the needle.
Figure 65:
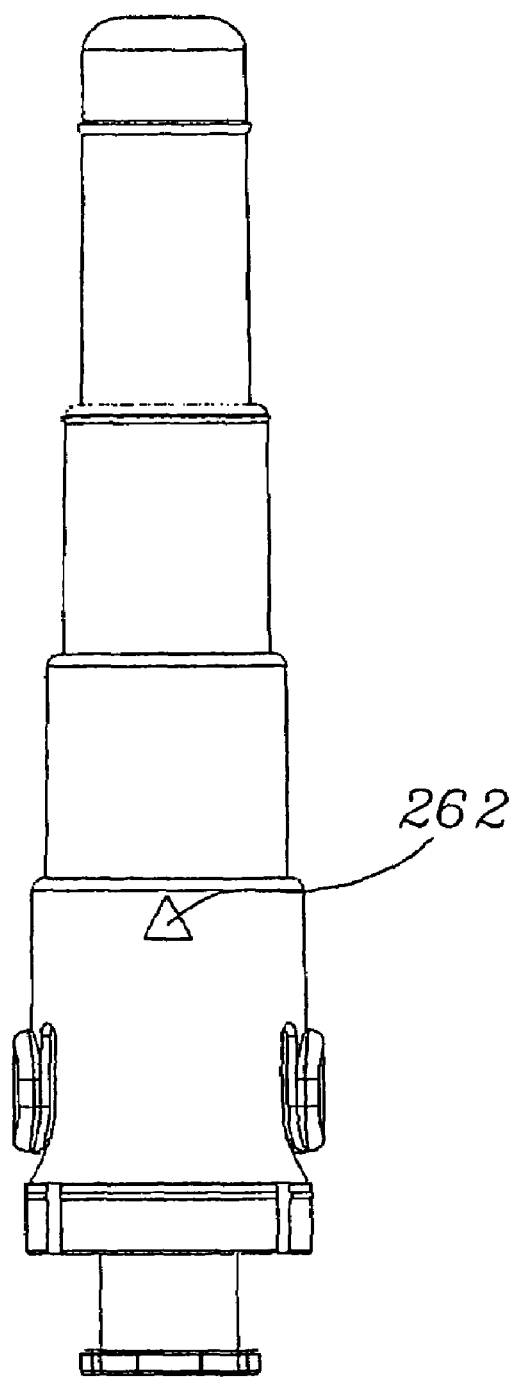

FIGS. 64 and 65 show another feature of the present invention. An identifying mark 262 may be placed on the needle shield 20 to show the orientation of the bevel 68 on the needle 24. The identifying mark 262 may be an ink mark, a molded textured surface, a molded in arrow, or a separate component attached to the device. This allows the user to easily orient the needle to the preferred orientation.

Figure 66:
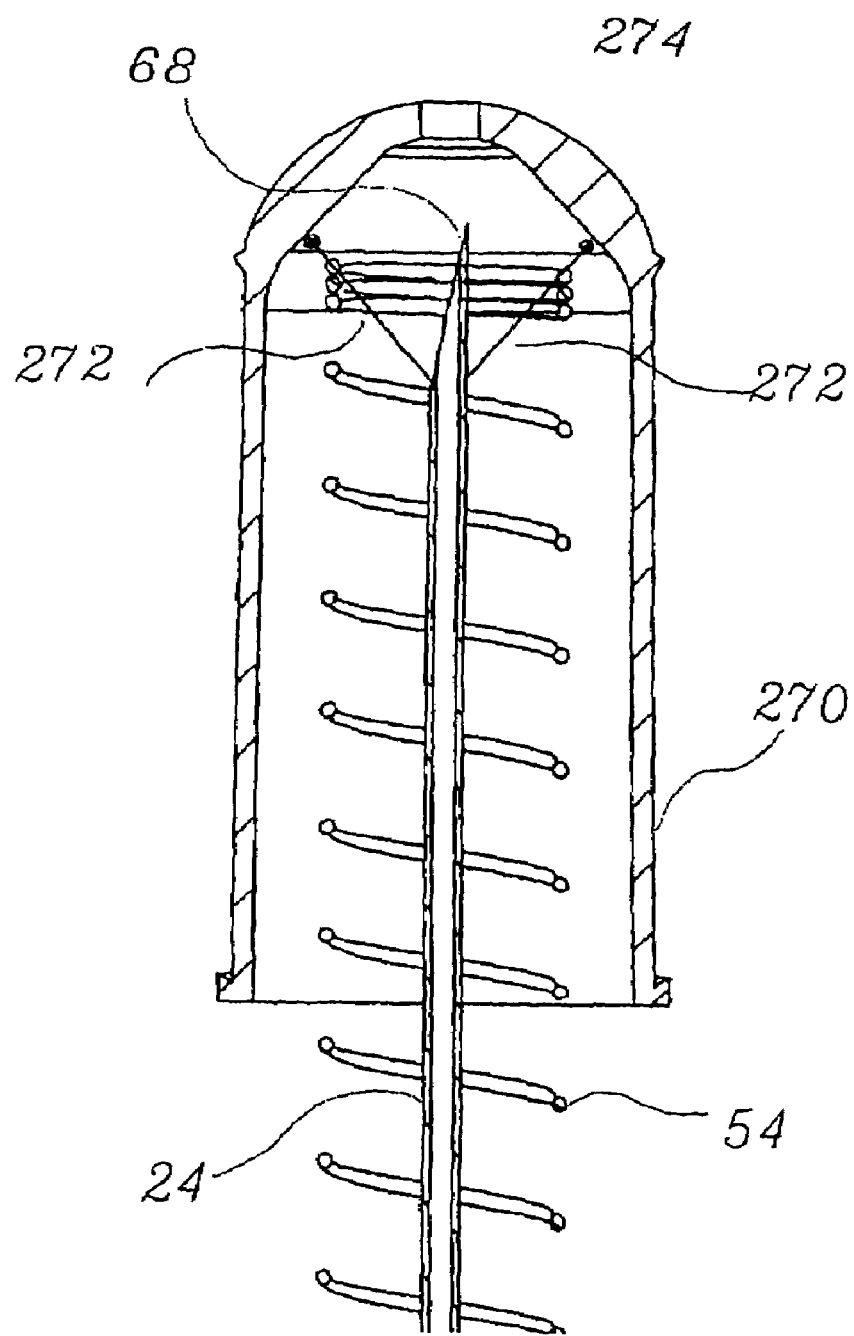
Figure 67:
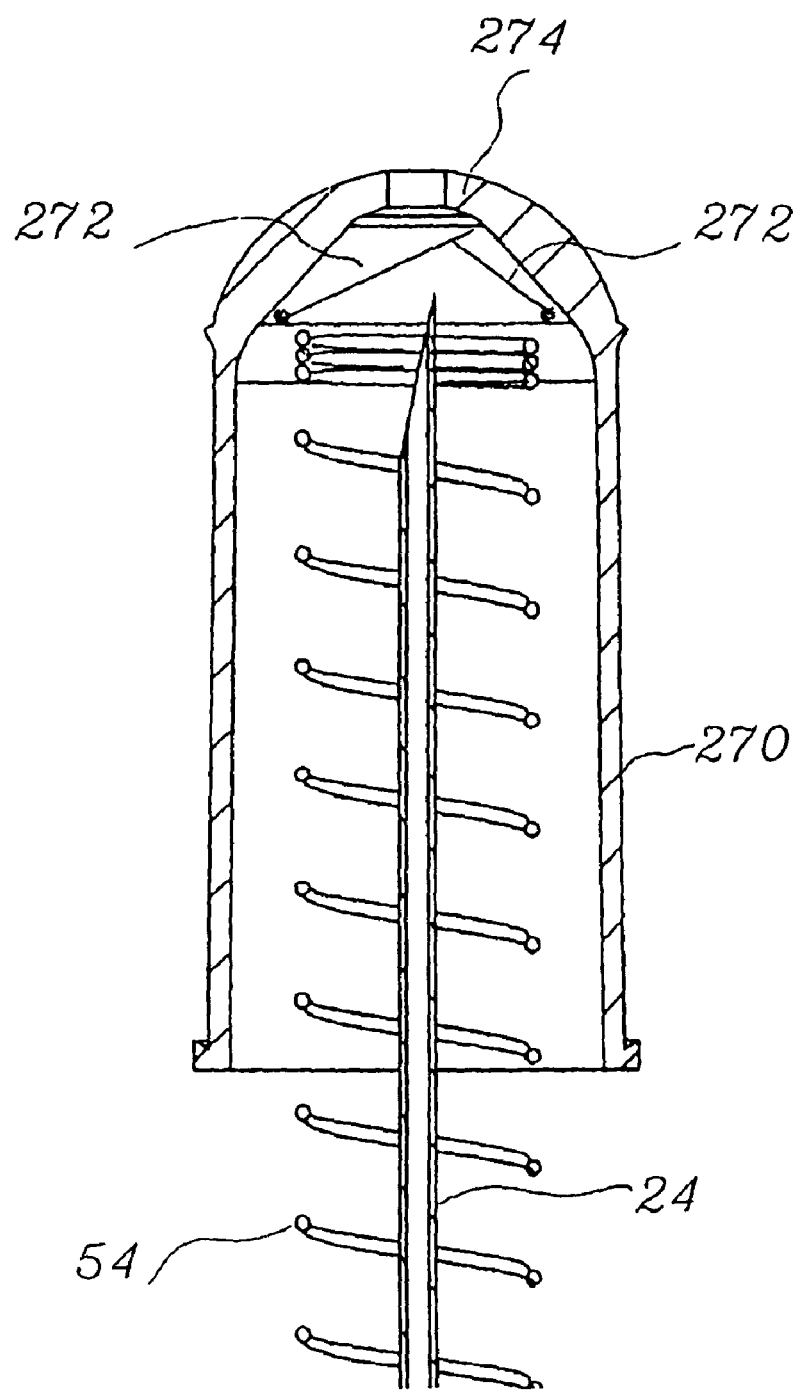

FIGS. 66 and 67 show an embodiment of the present invention with a two arm closing structure. In FIG. 66, a single cylindrical component 270 is shown as an alternative to the three cylindrical components shown before. The cylindrical component 270 is similar to those previously described, but is interacts with the latch mechanism allowing it to be released. In FIG. 66 the needle shield assembly 20 is shown just before the cylindrical component 270 moves past the end of the needle 24. The spring 54 is compressed between the needle hub 22 and the cylindrical component 270. The needle 24 extends from the needle hub 22 through the spring 54, through the two arms 272, and exits the needle shield assembly 20 through the hole 274 in the end of the cylindrical component 270.

This embodiment of the closing structure has two arms 272 near the end of the cylindrical component 270 extending inward toward the needle. The two arms 272 are bend downward and with spring action rest against the needle 24 that passes through the two downwardly bent arms 272.

The needle shield 20 using the two arms 272 operates as follows. A user places the needle 24 under the skin and then depresses the actuation pads 74 that pivot the latches 38 releasing the cylindrical component 270. The compressed spring 54 expands pushing the cylindrical component 270 in a direction along the needle 24. Once the spring 54 has completely expanded, the cylindrical component 270 has extended beyond the end 68 of the needle 24, and the end of the needle 68 is then completely enclosed within the needle shield assembly 20. Once the spring 54 has moved the two arms 272 beyond the end 68 of the needle 24, the two arms 272 move upward due to the spring force of the arms 272 as seen fin FIG. 67. The arms 272 block the needle, and thus prevents the end 68 of the needle 24 from exiting the needle shield assembly 20 again. The two arms may be made of metal or any other elastic material. Also, the two strips could be made of a rigid material, in which case a spring mechanism could be used to cause the two arms to spring upward once they have passed the end of the needle.

Figure 68:
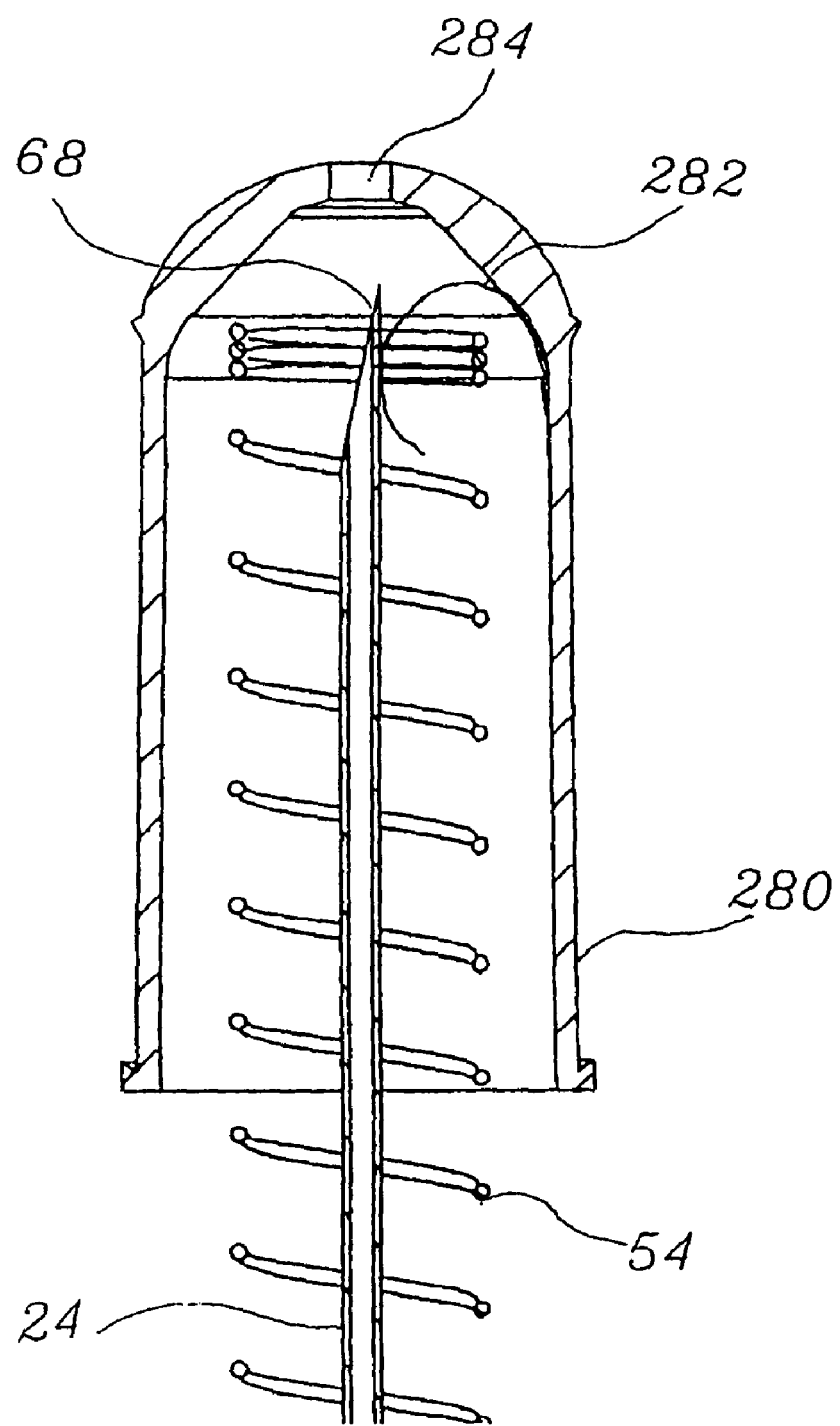
Figure 69:
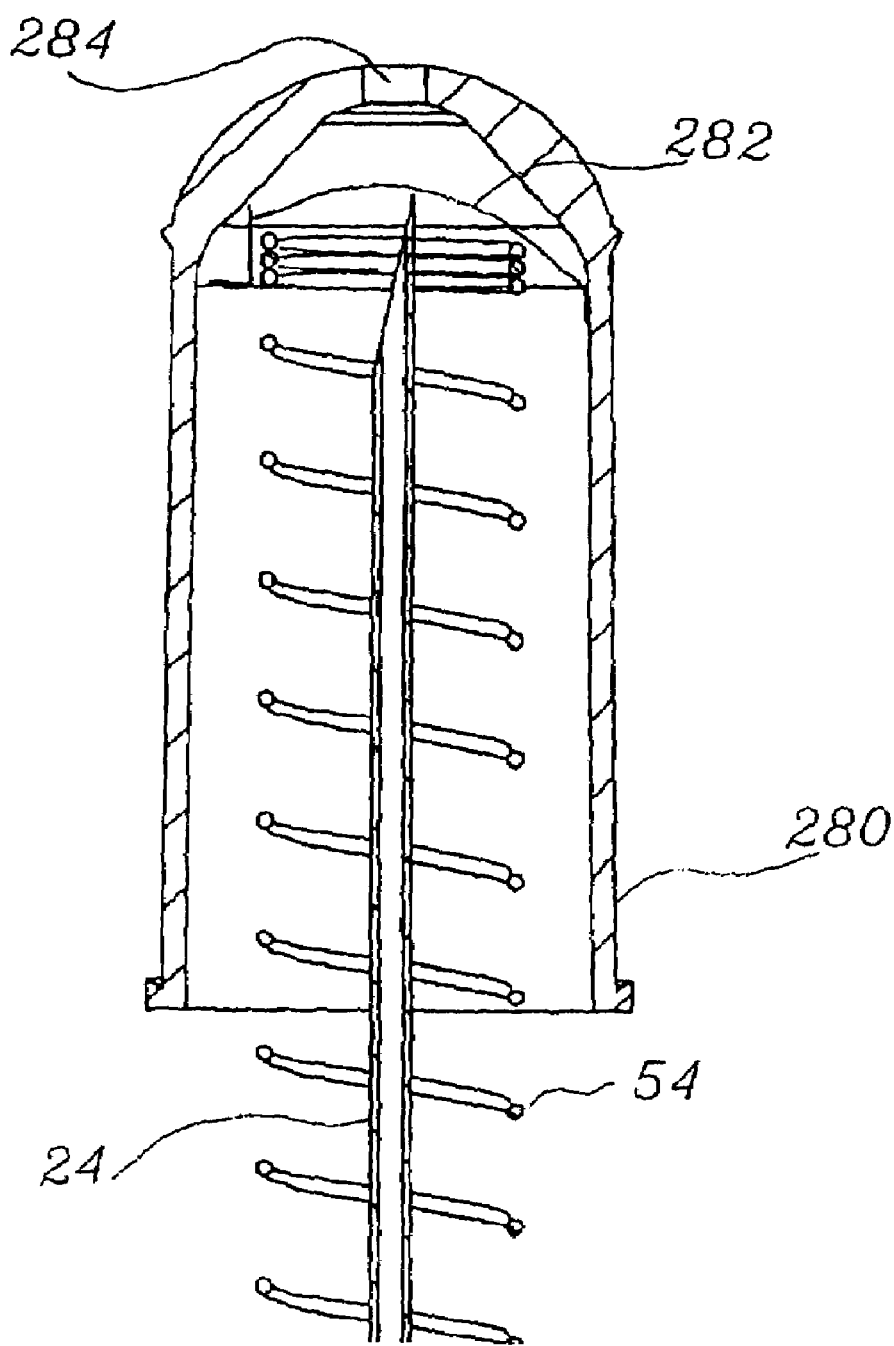

FIGS. 68 and 69 show an embodiment of the present invention with a strip closing structure. In FIG. 68, a single cylindrical component 280 is shown as an alternative to the three cylindrical components shown before. The cylindrical component 270 is similar to those previously described, but is interacts with the latch mechanism allowing it to be released. In FIG. 68 the needle shield assembly 20 is shown just before the cylindrical component 280 moves past the end of the needle 24. The spring 54 is compressed between the needle hub 22 and the cylindrical component 280. The needle 24 extends from the needle hub 22 through the spring 54, past the strip 282, and exits the needle shield assembly 20 through the hole 284 in the end of the cylindrical component 280.

This embodiment of the closing structure has a strip 282 near the end of the cylindrical component 270 curled downward and inward toward the needle 24. The strip 282 rests rest against the needle 24 with a spring action. The strip may be made of metal or any other elastic material.

The needle shield 20 using the strip 282 operates as follows. A user places the needle 24 under the skin and then depresses the actuation pads 74 that pivot the latches 38 releasing the cylindrical component 280. The compressed spring 54 expands pushing the cylindrical component 280 in a direction along the needle 24. Once the spring 54 has completely expanded, the cylindrical component 280 has extended beyond the end 68 of the needle 24, and the end of the needle 68 is then completely enclosed within the needle shield assembly 20. Once the spring 54 has moved the strip 282 beyond the end 68 of the needle 24, the strip 272 moves upward due to the spring force of the strip 282 as seen fin FIG. 69. The strip 282 blocks the needle 24, and thus prevents the end 68 of the needle 24 from exiting the needle shield assembly 20 again.

One of the advantages of the present inventions is that it can be used with one hand. Many of the prior art solutions required the use of two hands to protect the needle. The location of the latch structure near the end of the syringe allows a users to easily over their fingers to release the latches. This causes the closing structure to move towards the end of the needle, and then the closing structure and needle shield encloses the end of the needle 24 when the needle is withdrawn from the patient, thus preventing unintentional needle sticks with a used needle.

It will be apparent to those skilled in the art that various modifications and variation can be made in the present invention without departing from the spirit or scope of the invention. For example, the single cylindrical member embodiment shown in FIGS. 66–69 may be used with any of the closing structures described herein. Also, cylindrical members are described, but elongated members with other cross sections and even varying cross sections may be used to implement the present invention. Thus, it is intended that the present invention cover the modifications and variations of this invention provided they come within the scope of the appended claims and their equivalents.

What is claimed:
1. A safety needle comprising:
   a needle with a sharp end; and
   a needle shield comprising:
      collapsible interlocking members, wherein one member is an end member with a hole surrounding the needle;
      a spring inside the collapsible interlocking members that applies an expanding force on the collapsible interlocking members;
      a releasable latch structure that retains the collapsible interlocking members in a collapsed state, wherein when the releasable latch structure is actuated the collapsible interlocking members expand and enclose the sharp end of the needle; and a closing structure, including a slide cap that includes a hole and a tubular structure engaging the spring and includes a sloped end that engages a ramp on the inside of the end member, that prevents the sharp end of the needle from exiting the hole after the collapsible interlocking members encloses the sharp end of the needle.

2. A safety needle comprising:
a needle with a sharp end and a base;
and a needle shield comprising:
   a member with a hole surrounding the needle;
   a spring inside the member that applies an expanding force on the member;
   a retaining structure that retains the member near the base of the needle, wherein when the retaining structure is actuated the spring expands and encloses the sharp end of the needle with the member; and
   a closing structure that prevents the sharp end of the needle from exiting the hole after the member encloses the sharp end of the needle, wherein the closing structure includes a slide cap with a hole and a tubular structure engaging the spring and includes a sloped end that engages a ramp on the inside of the end member.

* * * * *